(12) United States Patent
Scheib

(10) Patent No.: US 11,607,218 B2
(45) Date of Patent: Mar. 21, 2023

(54) TRANSLATABLE BARREL CAM OF A ROBOTIC SURGICAL SYSTEM

(71) Applicant: Cilag GmbH International, Zug (CH)

(72) Inventor: Charles J. Scheib, Loveland, OH (US)

(73) Assignee: Cilag GmbH International, Zug (CH)

( * ) Notice: Subject to any disclaimer, the term of this patent is extended or adjusted under 35 U.S.C. 154(b) by 118 days.

(21) Appl. No.: 17/245,100

(22) Filed: Apr. 30, 2021

(65) Prior Publication Data

US 2022/0346780 A1 Nov. 3, 2022

(51) Int. Cl.
*A61B 17/072* (2006.01)
*A61B 34/00* (2016.01)
(Continued)

(52) U.S. Cl.
CPC ...... *A61B 17/072* (2013.01); *A61B 17/07207* (2013.01); *A61B 34/70* (2016.02); *B25J 9/102* (2013.01); *B25J 9/109* (2013.01); *F16H 25/20* (2013.01); *A61B 17/00234* (2013.01); *A61B 34/30* (2016.02); *A61B 90/50* (2016.02); *A61B 2017/00367* (2013.01);
(Continued)

(58) Field of Classification Search
CPC .............. A61B 17/068; A61B 17/072; A61B 17/07207; A61B 17/115; A61B 17/00234; A61B 17/1285; A61B 17/3201; A61B 17/29; A61B 2017/07214; A61B 2017/07257; A61B 2017/00367; A61B 2017/2927; A61B 2017/2929; A61B 34/20; A61B 34/30; A61B 34/37; A61B 34/70; A61B 34/71; A61B 18/1442; A61B 90/50; A61B 90/57; F16H 25/186; F16H 25/20; F16H 57/0025

USPC .......... 227/19, 175.1, 175.2, 176.1; 600/567, 600/568, 566; 606/1, 139, 130, 219; 901/19, 27

See application file for complete search history.

(56) References Cited

U.S. PATENT DOCUMENTS 6,451,027 B1 * 9/2002 Cooper .............. A61B 1/00149
901/19
7,404,508 B2 7/2008 Smith et al.
(Continued)

OTHER PUBLICATIONS

U.S. Appl. No. 17/022,520, entitled "Method of Applying Buttress to End Effector of Surgical Stapler," filed Sep. 19, 2020.
(Continued)

*Primary Examiner* — Scott A Smith
(74) *Attorney, Agent, or Firm* — Frost Brown Todd LLP

(57) ABSTRACT

A surgical instrument including an end effector, a shaft assembly defining a longitudinal axis extending proximally from the end effector, a first drive operatively connected to a first portion of at least one of the end effector or the shaft assembly, and an activating mechanism operatively connected to the first drive. The first drive longitudinally translates relative to the longitudinal axis from a first drive position toward a second drive position to respectively actuate the first portion from a first portion position toward a second portion. The activating mechanism selectively direct translation of the first drive from the first drive position toward the second drive position by rotating from a first rotational body position toward a second rotational body position or translating from a first translational body position toward a second translational body position.

20 Claims, 12 Drawing Sheets

(51) Int. Cl.
*B25J 9/10* (2006.01)
*F16H 25/20* (2006.01)
*A61B 17/00* (2006.01)
*A61B 34/30* (2016.01)
*A61B 90/50* (2016.01)
*F16H 25/18* (2006.01)
*F16H 57/00* (2012.01)

(52) U.S. Cl.
CPC .............. *A61B 2017/07214* (2013.01); *A61B 2017/07257* (2013.01); *F16H 25/186* (2013.01); *F16H 57/0025* (2013.01)

(56) References Cited

U.S. PATENT DOCUMENTS

| | | | |
|---|---|---|---|
| 7,434,715 B2 | 10/2008 | Shelton, IV et al. | |
| 7,721,930 B2 | 5/2010 | McKenna et al. | |
| 7,753,857 B2* | 7/2010 | Hibner | A61B 10/0283 600/566 |
| 7,828,748 B2* | 11/2010 | Hibner | A61B 10/0283 600/568 |
| 7,854,707 B2* | 12/2010 | Hibner | A61B 10/0275 600/567 |
| 8,052,615 B2* | 11/2011 | Reuber | A61B 10/0283 600/567 |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,663,220 B2 | 3/2014 | Wiener et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,949,785 B2 | 4/2018 | Price et al. | |
| 10,092,292 B2 | 10/2018 | Boudreaux et al. | |
| 10,349,939 B2 | 7/2019 | Shelton, IV et al. | |
| 2006/0079874 A1 | 4/2006 | Faller et al. | |
| 2006/0151567 A1* | 7/2006 | Roy | A61B 17/07207 227/19 |
| 2007/0032741 A1* | 2/2007 | Hibner | A61B 10/0283 600/566 |
| 2007/0191713 A1 | 8/2007 | Eichmann et al. | |
| 2008/0200940 A1 | 8/2008 | Eichmann et al. | |
| 2019/0000576 A1* | 1/2019 | Mintz | A61B 90/57 |
| 2021/0015572 A1* | 1/2021 | Gomez | A61B 34/35 |
| 2021/0022815 A1* | 1/2021 | Abbott | A61B 34/71 |
| 2021/0393340 A1 | 12/2021 | Beckman et al. | |

OTHER PUBLICATIONS

U.S. Appl. No. 17/077,067, entitled "Surgical Instrument and Carrier KART Supporting Ultrasonic Transducer," filed Oct. 22, 2020.
U.S. Appl. No. 17/077,086, entitled "Carrier KART and Jaw Closure of an Ultrasonic Surgical Instrument," filed Oct. 22, 2020.
U.S. Appl. No. 17/076,956, entitled "Surgical Instrument with an Articulatable Shaft Assembly and Dual End Effector Role," filed Oct. 22, 2020.
U.S. Appl. No. 17/076,959, entitled "Ultrasonic Surgical Instrument with a Distally Grounded Acoustic Wave," filed Oct. 22, 2020.
U.S. Appl. No. 17/077,098, entitled "Ultrasonic Surgical Instrument with a Multiplanar Articulation Joint," filed Oct. 22, 2020.
U.S. Appl. No. 17/077,110, entitled "Ultrasonic Surgical Instrument with a Mid-Shaft Closure System and Related Methods," filed Oct. 22, 2020.
U.S. Appl. No. 17/077,130, entitled "Surgical Instrument with Clamping Sensor Feedback and Related Methods," filed Oct. 22, 2020.
U.S. Appl. No. 17/077,136, entitled "Surgical Instrument with Non-Clamping Sensor Feedback and Related Methods," filed Oct. 22, 2020.
U.S. Appl. No. 17/077,139, entitled "Ultrasonic Surgical Instrument with a Fixed Transducer Grounding," filed Oct. 22, 2020.
U.S. Appl. No. 17/077,146, entitled "Ultrasonic Surgical Instrument with a Shaft Assembly and Elongated Waveguide Support Arrangement," filed Oct. 22, 2020.
U.S. Appl. No. 17/077,152, entitled "Damping Rings for an Ultrasonic Surgical Instrument," filed Oct. 22, 2020.
U.S. Appl. No. 17/077,250, entitled "Ultrasonic Surgical Instrument with a Carrier KART and Reusable Stage," filed Oct. 22, 2020.
U.S. Appl. No. 17/077,373, entitled "Surgical Instrument with a Carrier KART and Various Communication Cable Arrangements," filed Oct. 22, 2020.
U.S. Appl. No. 17/245,111, entitled "Selectable Jaw Closure of a Robotic Surgical System," filed Apr. 30, 2021.
U.S. Appl. No. 17/245,332, entitled "Variable Jaw Closure of a Robotic Surgical System," filed Apr. 30, 2021.
U.S. Appl. No. 17/245,340, entitled "Robotic Surgical System with an Articulation Lockout," filed Apr. 30, 2021.
U.S. Appl. No. 17/245,351, entitled "Multi-Zone Jaw Closure of a Robotic Surgical System," filed Apr. 30, 2021.

* cited by examiner

TRANSLATABLE BARREL CAM OF A ROBOTIC SURGICAL SYSTEM

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. patents is incorporated by reference herein in its entirety.

Additional examples of such surgical instruments include an ultrasonic surgical instrument with end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned; U.S. Pub. No. 2007/0191713, entitled "Ultrasonic Device for Cutting and Coagulating," published Aug. 16, 2007, now abandoned; U.S. Pub. No. 2008/0200940, entitled "Ultrasonic Device for Cutting and Coagulating," published Aug. 21, 2008, now abandoned, U.S. Pat. No. 9,949,785, entitled "Ultrasonic Surgical Instrument with Electrosurgical Feature," issued Apr. 24, 2018; and U.S. Pat. No. 8,663,220, entitled "Ultrasonic Surgical Instruments," issued Mar. 4, 2014. The disclosure of each of the above-cited U.S. patent Publications and U.S. patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
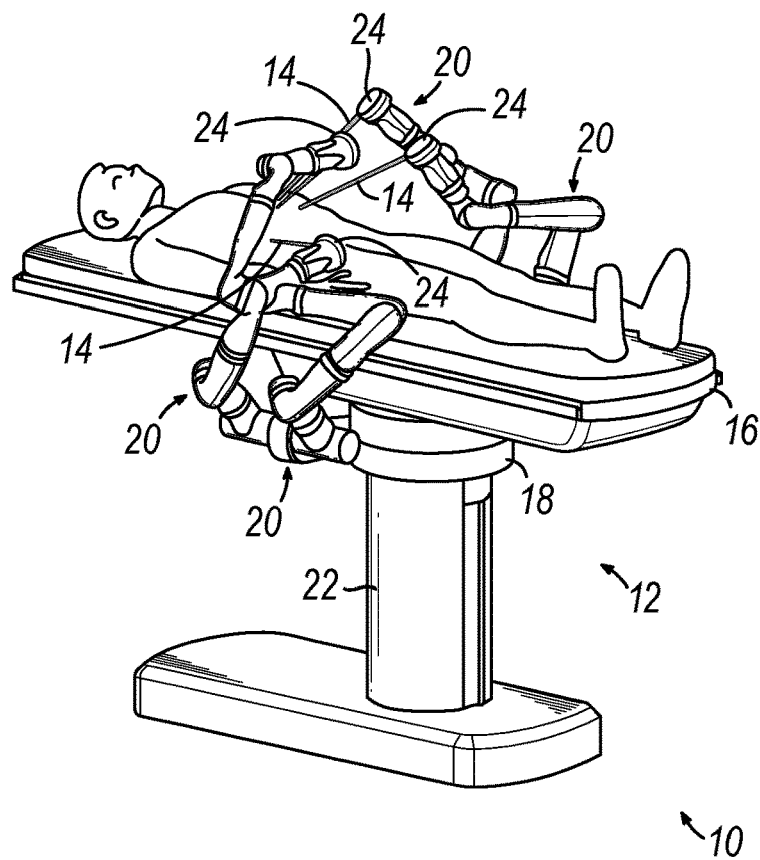
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "longitudinal," "inner," "outer," and "upper," also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. Exemplary Robotically-Enabled Medical System

FIG. 1 shows an exemplary robotically-enabled medical system, including a first example of a table-based robotic system (10). Table-based robotic system (10) of the present example includes a table system (12) operatively connected to a surgical instrument (14) for a diagnostic and/or therapeutic procedure in the course of treating a patient. Such procedures may include, but are not limited to, bronchoscopy, ureteroscopy, a vascular procedure, and a laparoscopic procedure. To this end, surgical instrument (14) is configured for a laparoscopic procedure, although it will be appreciated that any instrument for treating a patient may be similarly used. At least part of table-based robotic system (10) may be constructed and operable in accordance with at least some of the teachings of any of the various patents, patent application publications, and patent applications that are cited herein.

A. First Exemplary Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Exemplary Table-Based Robotic System

Figure 2:
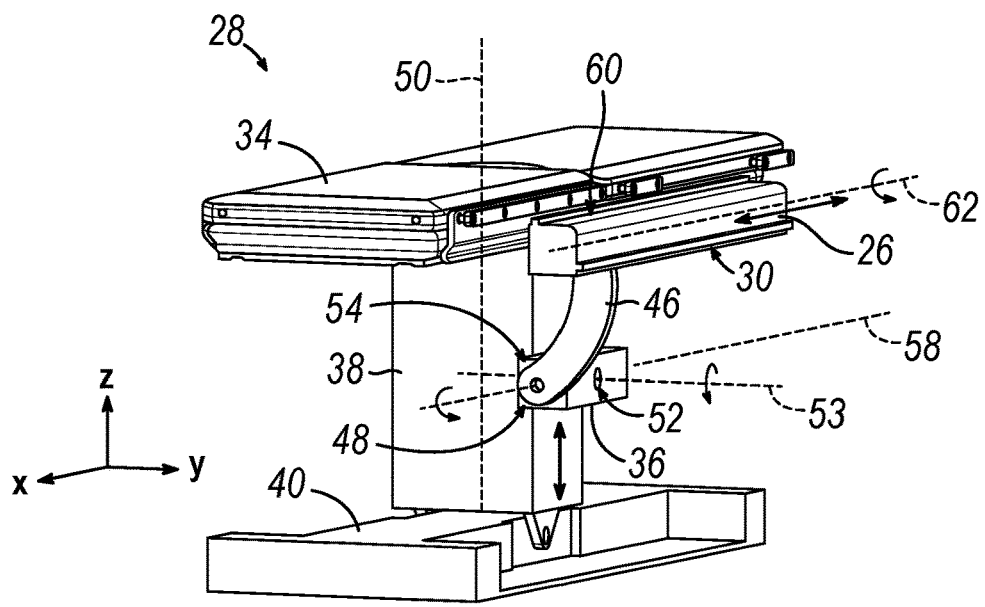
FIG. 2 depicts a perspective view of a second example of a table-based robotic system.
Figure 3:
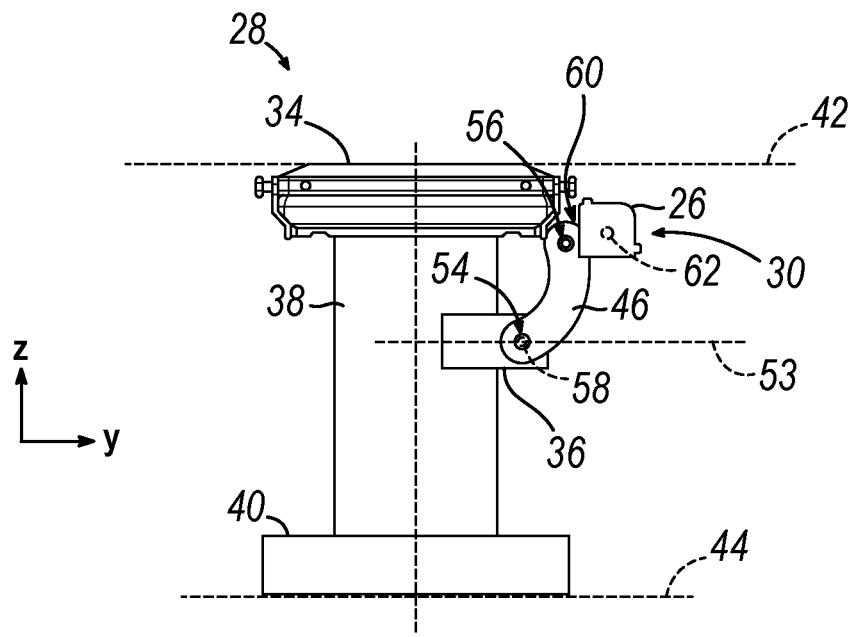
FIG. 3 depicts an end elevational view of the table-based robotic system of FIG. 2.
Figure 4:
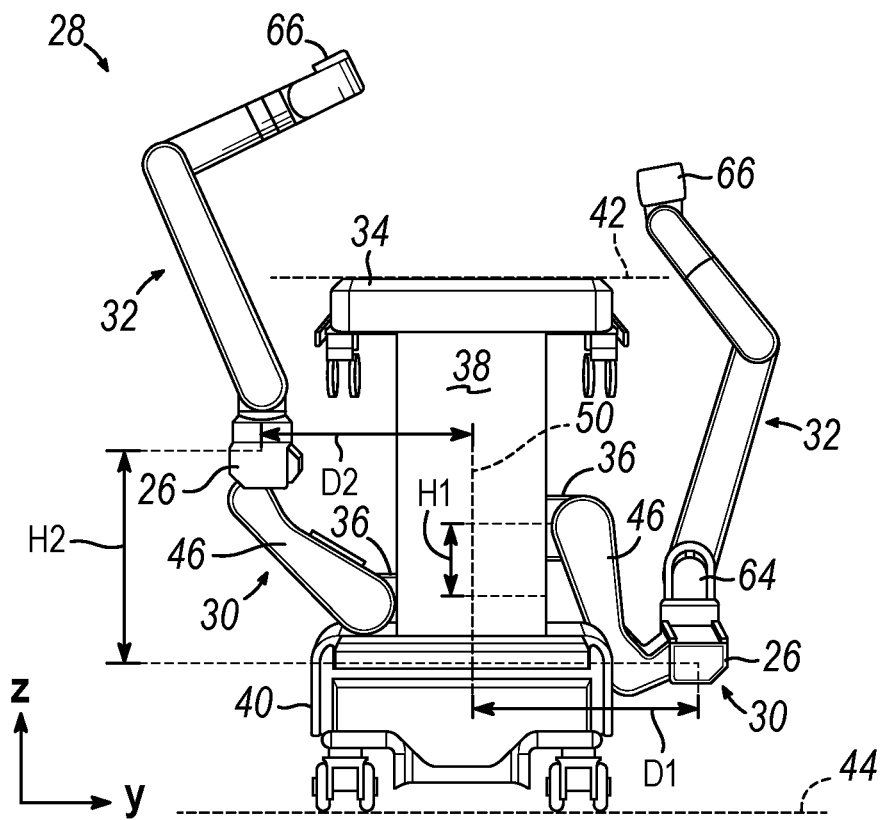
FIG. 4 depicts the end elevational view of the table-based robotic system of FIG. 3 including a pair of exemplary robotic arms.

As discussed briefly above, a second exemplary table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw, and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as surgical instrument (14) (see FIG. 6A), the instrument includes an instrument-based insertion architecture.

Figure 5:
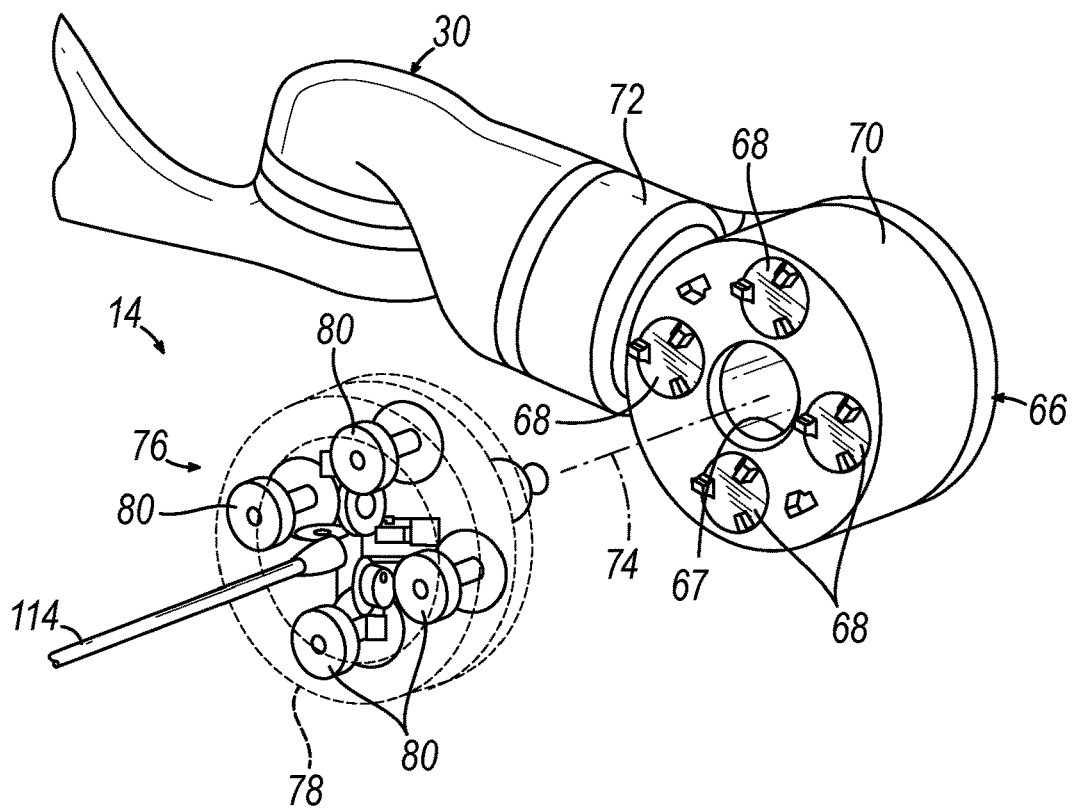
FIG. 5 depicts a partially exploded perspective view of the robotic arm of FIG. 4 having an instrument driver and a first exemplary surgical instrument.

FIG. 5 shows one example of instrument driver (66) in greater detail with surgical instrument (14) removed therefrom. Given the present instrument-based insertion architecture shown with reference to surgical instrument (14), instrument driver (66) further includes a clearance bore (67) extending entirely therethrough so as to movably receive a portion of surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of surgical instrument (14). Instrument driver (66) and surgical instrument (14) of the present example are aligned such that the axes of each drive output (68) are parallel to the axis of surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with surgical instrument (14) as a single unit around an instrument driver axis (74).

Any systems described herein, including table-based robotic system (28), may further include an input controller (not shown) for manipulating one or more instruments (not shown). In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller (not shown) such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. Exemplary Surgical Instrument

Figure 6A:
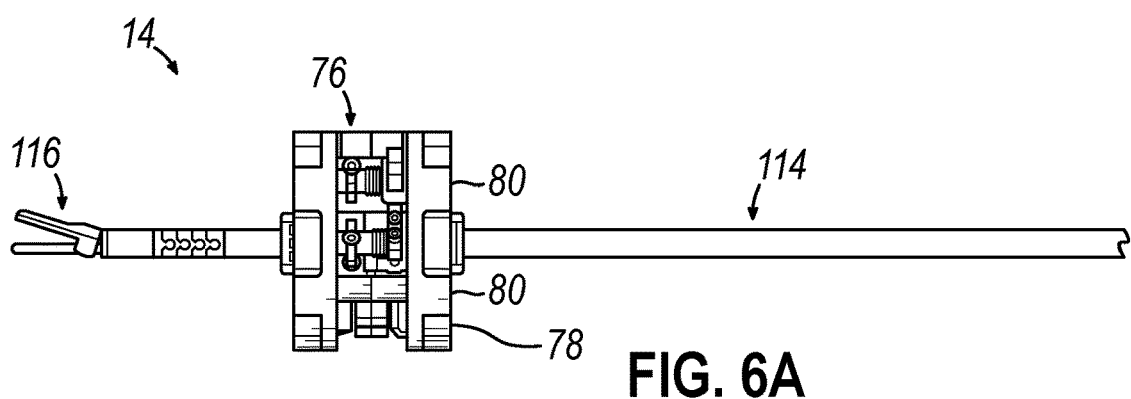
FIG. 6A depicts a side elevational view of the surgical instrument of FIG. 5 in a retracted position.
Figure 6B:
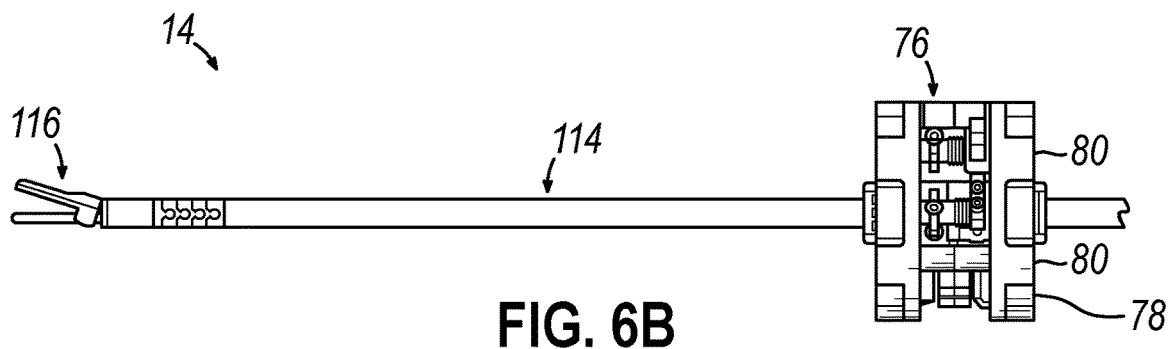
FIG. 6B depicts the side elevational view the surgical instrument similar to FIG. 6A, but in an extended position.

With respect to FIGS. 5-6B and in cooperation with instrument driver (66) discussed above, surgical instrument (14) includes an elongated shaft assembly (114) and an instrument base (76) with an attachment interface (78) having a plurality of drive inputs (80) configured to respectively couple with corresponding drive outputs (68). Shaft assembly (114) of ultrasonic surgical instrument (14) extends from a center of instrument base (76) with an axis substantially parallel to the axes of the drive inputs (80) as discussed briefly above. With shaft assembly (114) positioned at the center of instrument base (76), shaft assembly (114) is coaxial with instrument driver axis (74) when attached and movably received in clearance bore (67). Thus, rotation of rotational assembly (70) causes shaft assembly (114) of surgical instrument (14) to rotate about its own longitudinal axis while clearance bore (67) provides space for translation of shaft assembly (114) during use.

To this end, FIGS. 5-6B show surgical instrument (14) having the instrument-based insertion architecture as discussed briefly above. Surgical instrument (14) includes elongated shaft assembly (114), end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by ultrasonic surgical instrument (14), although it will be appreciated that such insertion into and withdrawal may also occur via adjustable arm supports (30) in one or more examples.

While the present example of instrument driver (66) shows drive outputs (68) arranged in rotational assembly

(70) so as to face in a distal direction like distally projecting end effector (116) from shaft assembly (114), an alternative instrument driver (not shown) may include drive output (68) arranged on an alternative rotational assembly (70) to face in a proximal direction, opposite of the distally projecting end effector (116). In such an example, surgical instrument (14) may thus have drive inputs (80) facing distally to attach to instrument drivers (66) facing proximally in an opposite direction from that shown in FIG. 5. The invention is thus not intended to be unnecessarily limited to the particular arrangement of drive outputs (68) and drive inputs (80) shown in the present example and any such arrangement for operatively coupling between drive outputs and inputs (68, 80) may be similarly used.

While various features configured to facilitate movement between end effector (116) and drive inputs (80) are described herein, such features may additionally or alternatively include pulleys, cables, carriages, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

II. Exemplary Surgical Stapler

In some instances, it may be desirable to use various alternative surgical instruments with robotic systems (10, 28) described above in addition to, or in lieu of, surgical instrument (14). Such alternative surgical instruments may be desirable to provide improved operability when used with robotic systems (10, 28). For instance, as described above, surgical instrument (14) may move between a retracted position and extended position. Additionally, it may be beneficial to translate a portion of surgical instrument (14) along a support structure to provide increased surgical access without increasing the dimensions of surgical instrument (14). As also described above, use of rotational assembly (70) of robotic arm (20, 32) may enable rotation of the entire surgical instrument (14), rather than specific structures of surgical instrument (14) being rotatable.

One such example of these alternative surgical instruments includes a second exemplary surgical instrument (210), which may also be referred to as surgical stapler (210) and is discussed below in greater detail. Additional examples of alternative surgical instruments and/or associated features for incorporation with robotic systems (10, 28) are described in U.S. patent application Ser. No. 16/946,363, entitled "Articulation Mechanisms for Robotic Surgical Tools," filed on Jun. 18, 2020, published as U.S. Pub. No. 2021/0393340 on Dec. 23, 2021; U.S. patent application Ser. No. 17/077,067, entitled "Surgical Instrument and Carrier KART Supporting Ultrasonic Transducer," filed on Oct. 22, 2020, published as U.S. Pub. No. 2022/0125465 on Apr. 28, 2022; U.S. patent application Ser. No. 17/077,086, entitled "Carrier KART and Jaw Closure of an Ultrasonic Surgical Instrument," filed on Oct. 22, 2020, published as U.S. Pub. No. 2022/0125466 on Apr. 28, 2022; U.S. patent application Ser. No. 17/077,130, entitled "Surgical Instrument with Clamping Sensor Feedback and Related Methods," filed on Oct. 22, 2020, published as U.S. Pub. No. 2022/0125469 on Apr. 28, 2022; U.S. patent application Ser. No. 17/077,136, entitled "Surgical Instrument with Non-clamping Sensor Feedback and Related Methods," filed on Oct. 22, 2020, published as U.S. Pub. No. 2022/0125470 on Apr. 28, 2022; U.S. patent application Ser. No. 17/077,250, entitled "Ultrasonic Surgical Instrument with a Carrier KART and Reusable Stage," filed on Oct. 22, 2020, published as U.S. Pub. No. 2022/0125472 on Apr. 28, 2022; U.S. patent application Ser. No. 17/077,373, entitled "Surgical Instrument with a Carrier KART and Various Communication Cable Arrangements," filed on Oct. 22, 2020, published as U.S. Pub. No. 2022/0125473 on Apr. 28, 2022; U.S. patent application Ser. No. 17/077,139, entitled "Ultrasonic Surgical Instrument with a Fixed Transducer Grounding," filed on Oct. 22, 2020, published as U.S. Pub. No. 2022/0125471 on Apr. 28, 2022; U.S. patent application Ser. No. 17/077,146, entitled "Ultrasonic Surgical Instrument with a Shaft Assembly and Elongated Waveguide Support Arrangement," filed on Oct. 22, 2020, published as U.S. Pub. No. 2022/0125460 on Apr. 28, 2022; U.S. patent application Ser. No. 17/077,152, entitled "Damping Rings for an Ultrasonic Surgical Instrument," filed on Oct. 22, 2020, published as U.S. Pub. No. 2022/0125461 on Apr. 28, 2022; U.S. patent application Ser. No. 17/077,110, entitled "Ultrasonic Surgical Instrument with a Mid-shaft Closure System and Related Methods," filed on Oct. 22, 2020, published as U.S. Pub. No. 2022/0125468 on Apr. 28, 2022; U.S. patent application Ser. No. 17/076,956, entitled "Surgical Instrument with an Articulatable Shaft Assembly and Dual End Effector Roll," filed on Oct. 22, 2020, published as U.S. Pub. No. 2022/0125463 on Apr. 28, 2022; U.S. patent application Ser. No. 17/076,959, entitled "Ultrasonic Surgical Instrument with a Distally Grounded Acoustic Waveguide," filed on Oct. 22, 2020, published as U.S. Pub. No. 2022/0125464 on Apr. 28, 2022; and/or U.S. patent application Ser. No. 17/077,098, entitled "Ultrasonic Surgical Instrument with a Multiplanar Articulation Joint," filed on Oct. 22, 2020, published as U.S. Pub. No. 2022/0125467 on Apr. 28, 2022. The disclosure of each of the above-cited U.S. Patent Applications is incorporated by reference herein in its entirety. Various features of these alternative examples of surgical instruments may be readily incorporated into a surgical robotic system, such as robotic systems (10, 28), such that the invention is not intended to be unnecessarily limited to these particular alternative surgical instruments discussed herein.

A. Overview

Figure 7:
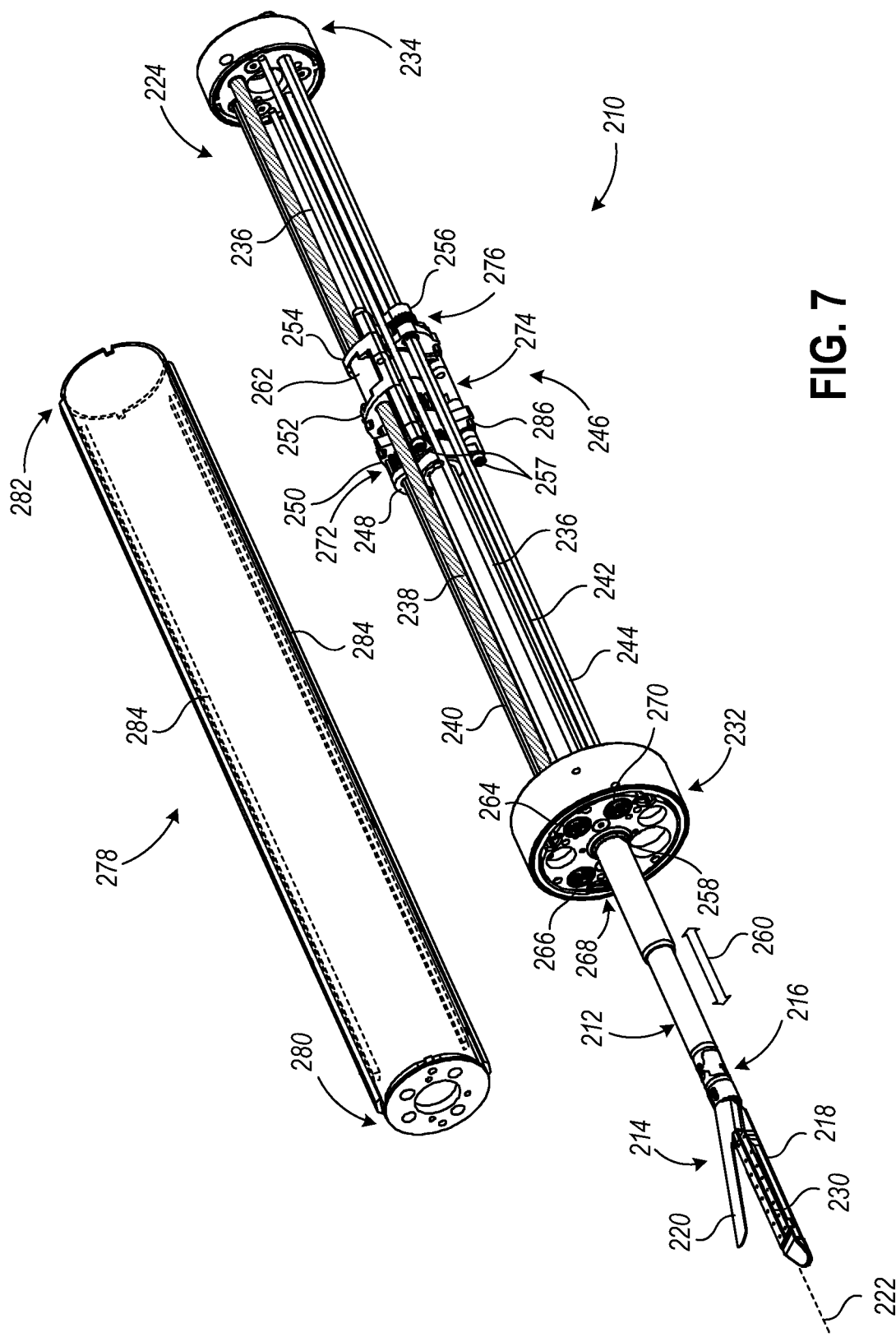
FIG. 7 depicts a perspective view of a second exemplary surgical instrument having a first example of a carriage operatively connected to an end effector configured for cutting and sealing transected tissue with a plurality of staples.

FIG. 7 is an exemplary surgical instrument (210) that may incorporate some or all of the principles of the present disclosure. Surgical instrument (210) may be similar in some respects to any of the instruments described above with reference to FIGS. 1-6B and, therefore, may be used in conjunction with a robotic surgical system, such as robotic systems (10, 28) of FIGS. 1-6B. As illustrated, surgical instrument (210) includes an elongated shaft (212), an end effector (214) arranged at a distal end of shaft (212), and an articulable wrist (216), which may also be referred to herein as a "wrist joint," that interposes and couples end effector (214) to the distal end of shaft (212).

Surgical instrument (210) can have any of a variety of configurations capable of performing one or more surgical functions. In the present example, end effector (214) comprises a surgical stapler, which may also be referred to herein as an "endocutter," configured to cut and staple tissue for fastening. As illustrated, end effector (214) includes opposing jaws (218, 220) configured to move, which may also be referred to as "articulate," between open and closed positions. Alternatively, end effector (214) may comprise other types of instruments requiring opposing jaws such as, but not limited to, other surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In another example, end effector (214) may instead comprise any end effector or instrument capable of being operated in conjunction with a robotic system, such as robotic systems (10, 28), and related methods. Such end effectors, and more generally instruments, include, but are not limited to, a suction irrigator, an endoscope (e.g., a camera), an ultrasonic instrument, an RF instrument, or any combination thereof.

One or both of jaws (218, 220) may be configured to pivot and actuate end effector (214) between open and closed positions. In the illustrated example, upper jaw (220) is rotatable, and more particularly pivotable, relative to lower jaw (218) to move between an open, unclamped position and a closed, clamped position. In other examples, however, lower jaw (218) may move relative to upper jaw (220). In still other examples, both lower and upper jaws (218, 220) may move to actuate end effector (214) between open and closed positions.

In the present example, lower jaw (218) is referred to as a "cartridge" or "channel" jaw, and upper jaw (220) is referred to as an "anvil" jaw. Lower jaw (218) may include a frame that houses or supports a staple cartridge, and upper jaw (220) is pivotally supported relative to upper jaw (220) and defines a surface that operates as an anvil to deform staples ejected from the staple cartridge during operation.

Wrist (216) enables end effector (214) to pivot relative to shaft (212) and thereby position end effector (214) at various desired orientations and locations relative to a surgical site. In the present example, wrist (216) is configured such that end effector (214) pivots laterally left and laterally right relative to a longitudinal axis (222) of shaft (212). In other examples, wrist (216) may alternatively provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a robotic surgical system (e.g., end effector (214)) with respect to a given reference Cartesian frame. As used herein, "surge" refers to forward and backward translational movement, "heave" refers to translational movement up and down, and "sway" refers to translational movement left and right. With regard to rotational terms, "roll" refers to tilting side to side, "pitch" refers to tilting forward and backward, and "yaw" refers to turning left and right.

Still referring to FIG. 7, surgical instrument (210) includes a drive housing (224) that houses an actuation system designed to facilitate articulation of wrist (216) and actuation of end effector (214) (e.g., clamping, firing, rotation, articulation, energy delivery, etc.). Drive housing (224), alternately referred to as a "stage," provides various coupling features that releasably couple surgical instrument (210) to an instrument driver of a robotic surgical system. Drive housing (224) includes a plurality of drive members (226, 228) (see FIG. 8A) that extend to wrist (216) and end effector (214). Selective actuation of one or more of drive members (226, 228) causes end effector (214) to pivot relative to shaft (212) at wrist (216). Selective actuation of one or more other drive members (not shown) causes end effector (214) to actuate, such as by closing and/or opening jaws (218, 220) and thereby enabling end effector (214) to clamp tissue. Once tissue is clamped between opposing jaws (218, 220), actuating end effector (214) may further include "firing" end effector (214), which may refer to causing a cutting element (not shown), such as a knife, to distally advance within a slot (230) defined in lower jaw (218). While moving distally, cutting element (not shown) transects tissue clamped between opposing jaws (218, 220). Moreover, as cutting element (not shown) advances, a plurality of staples (not shown) contained within staple cartridge (e.g., housed within lower jaw (218)) are urged into deforming contact with corresponding anvil surfaces, such as pockets, provided on upper jaw (220). In one example, the deployed staples may form multiple rows of staples configured to seal opposing sides of the transected tissue.

Drive housing (224) has a distal end (232) and an opposing, proximal end (234). Distal end (232) may also be referred to herein as a "handle." In some examples, one or more struts (236), such as two such struts (236), extend longitudinally between the distal and proximal ends (232, 234) to fix a distance between distal and proximal ends (232, 234), provide structural stability to drive housing (224), and secure distal end (232) relative to proximal end (234).

Drive housing (224) also includes a lead screw (238) and one or more splines (240, 242, 244), which also extend longitudinally between the distal and proximal ends (232, 234). In the present example, drive housing (224) includes a first spline (240), a second spline (242), and a third spline (244). While three splines (240, 242, 244) are depicted in the drive housing (224), more or less than three such splines (240, 242, 244) may be included in an alternative drive housing (224) in another example. Unlike struts (236), lead screw (238) and splines (240, 242, 244) are rotatably mounted to distal and proximal ends (232, 234). To this end, selective rotation of lead screw (238) and splines (240, 242, 244) causes various functions of drive housing (224) to transpire, such as translating end effector (214) along longitudinal axis (222), pivoting end effector (214) at wrist (216), opening or closing jaws (218, 220), and/or firing end effector (214).

Drive housing (224) further includes a carriage (246) movably mounted along lead screw (238) and splines (240, 242, 244) and houses various activating mechanisms configured to cause operation of specific functions of end effector (214). Carriage (246) may comprise two or more layers, shown in the present example as a first layer (248), a second layer (250), a third layer (252), a fourth layer (254), and a fifth layer (256). Lead screw (238) and splines (240, 242, 244) each extend through portions of one or more of layers (248, 250, 252, 254, 256) to allow carriage (246) to translate along longitudinal axis (222) with respect to lead screw (238) and splines (240, 242, 244). In some examples, layers (248, 250, 252, 254, 256) may be secured to each other in series using one or more mechanical fasteners (257) extending between first layer (248) and fifth layer (256) and through coaxially aligned holes defined in some or all of layers (248, 250, 252, 254, 256). While five layers (248, 250, 252, 254, 256) are shown in the present example, more or less than five such layers may be included in an alternative carriage (246) such that the invention is not intended to be unnecessarily limited to five layers (248, 250, 252, 254, 256).

Shaft (212) is coupled to and distally extends from carriage (246) through a central aperture (258) in distal end (232). Carriage (246) is movable between distal and proximal ends (232, 234) along longitudinal axis (222) and is thereby able to advance or retract end effector (214) relative to drive housing (224), as indicated by the arrows (260). More specifically, in some examples, carriage (246) includes a carriage nut (262) mounted to lead screw (238) and secured between third and fourth layers (252, 254). The outer surface of lead screw (238) defines outer helical threading and carriage nut (262) defines corresponding internal helical threading configured to be received within outer helical threading. As a result, rotation of lead screw (238) causes carriage nut (262) to advance or retract carriage (246) along longitudinal axis (222) and correspondingly advance or retract end effector (214) relative to drive housing (224).

As indicated above, lead screw (238) and splines (240, 242, 244) are rotatably mounted to distal and proximal ends (232, 234). More specifically, distal end (232) of drive housing (224) may include one or more rotatable drive inputs actuatable to independently rotate lead screw (238) and splines (240, 242, 244). In the present example, drive housing (224) includes a first drive input (264), a second drive input (266), a third drive input (268), and a fourth drive input (270). As described below, each drive input (264, 266, 268, 270) may be mateable with a corresponding drive output of an instrument driver such that rotation of a given drive output correspondingly rotates the associated drive input (264, 266, 268, 270) and thereby rotates the mated lead screw (238) or spline (240, 242, 244). While four drive inputs (264, 266, 268, 270) are shown in the present example, more or less than four may be included in an alternative drive housing such that the invention is not intended to be unnecessarily limited to four such drive inputs (264, 266, 268, 270).

First drive input (264) as shown is operatively coupled to lead screw (238) such that rotation of first drive input (264) correspondingly rotates lead screw (238), which causes carriage nut (262) and carriage (246) to advance or retract along longitudinal axis (222), depending on the rotational direction of lead screw (238). Second drive input (266) as shown is operatively coupled to first spline (240) such that rotation of second drive input (266) correspondingly rotates first spline (240). In one example, first spline (240) is operatively coupled to a first activating mechanism (272) of carriage (246), and first activating mechanism (272), in turn, is operable to open and close jaws (218, 220). Third drive input (268) as shown is operatively coupled to second spline (242) such that rotation of third drive input (268) correspondingly rotates second spline (242). In one example, second spline (242) is operatively coupled to a second activating mechanism (274) of carriage (246), and second activating mechanism (274) is operable to articulate end effector (214) at wrist (216). Fourth drive input (270) as shown is operatively coupled to third spline (244) such that rotation of fourth drive input (270) correspondingly rotates third spline (244). In one example, third spline (244) is operatively coupled to a third activating mechanism (276) of carriage (246), and third activating mechanism (276) is operable to fire cutting element (not shown) of end effector (214).

Drive housing (224) of the present example also includes a shroud (278) sized to receive and otherwise surround carriage (246), lead screw (238), and splines (240, 242, 244). Shroud (278) comprises a tubular structure having a distal end (280) mateable with distal end (232) of drive housing (224), and a proximal end (282) mateable with proximal end (234) of drive housing (224). Rails (284) extend longitudinally and parallel to lead screw (238) and are sized to be received within corresponding notches (286) defined on an outer periphery of carriage (246) and, more particularly, on the outer periphery of one or more of carriage layers (248, 250, 252, 254, 256). As carriage (246) translates along longitudinal axis (222), rails (284) are configured to maintain an angular position of carriage (246) and bear any torsional loading that may otherwise adversely affect movement and/or operation of carriage (246) during use.

Figure 8A:
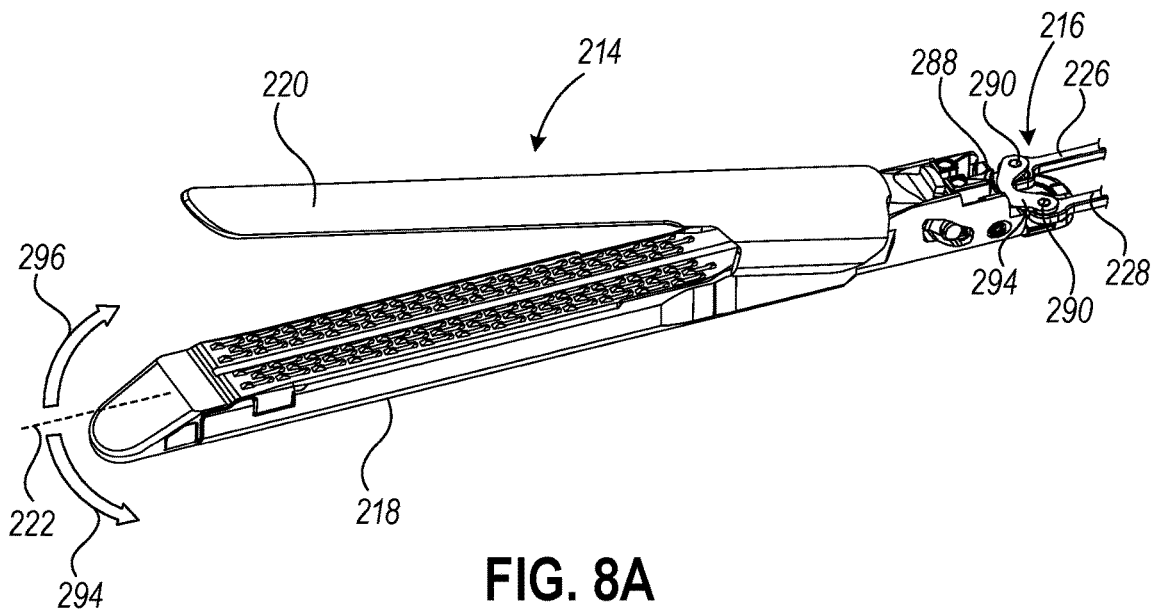
FIG. 8A depicts an enlarged perspective view of the end effector of FIG. 7 showing a wrist configured to articulate the end effector.

As shown in FIG. 8A, wrist (216) more particularly has drive members (226, 228) interconnected with end effector (214) and configured to articulate end effector (214) relative to longitudinal axis (222). End effector (214) is mounted to an end effector mount (288) having two articulation pins (290), and a distal end of each drive member (226, 228) is rotatably mounted to a corresponding one of articulation pins (290). Drive members (226, 228) are also interconnected at distal ends via a distal link (292), which together comprise a linkage configured to support articulation of end effector mount (288) and, in turn, articulation of end effector (214).

Drive members (226, 228) translate antagonistically and parallel along longitudinal axis (222), such that as first drive member (226) moves distally second drive member (228) moves proximally, and vice versa. Moreover, distal movement of first drive member (226) and simultaneous proximal movement of second drive member (228) cooperatively act on end effector mount (288) to cause end effector (214) to rotate counterclockwise, as indicated by an arrow (294). In contrast, proximal movement of first drive member (226) and simultaneous distal movement of second drive member (228) cooperatively act on end effector mount (288) to cause end effector (214) to rotate clockwise, as indicated by an arrow (296).

Figure 8B:
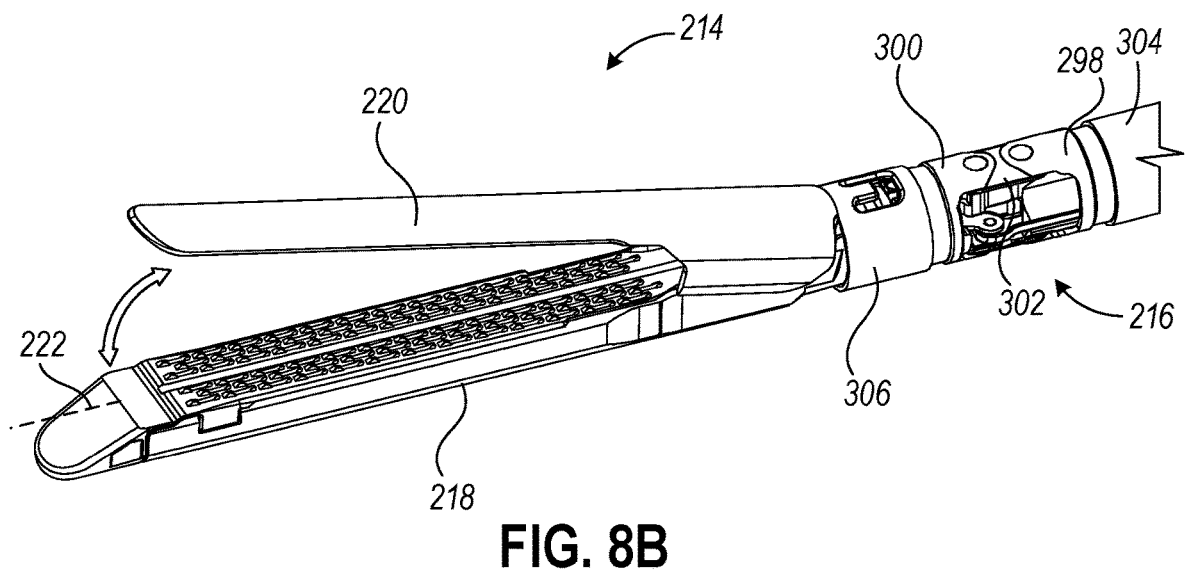
FIG. 8B depicts the enlarged perspective view of the end effector similar to FIG. 8A, but showing an upper jaw configured to selectively move between open and closed positions relative to a lower jaw.

FIG. 8B shows end effector (214) having jaws (218, 220) configured to selectively move between open and closed positions. To this end, wrist (216) has a proximal clevis (298), distal clevis (300), and a closure link (302) configured to operatively couple proximal and distal devises (298, 300) across wrist (216). Proximal clevis (298) of the present example is coupled a distal end of a closure tube (304) whereas distal clevis (300) is coupled to a closure ring (306). Axial movement of closure tube (304) along longitudinal axis (222) correspondingly moves proximal clevis (298) in the same axial direction, and closure link (302) is configured to transmit the axial load through wrist (216) to close jaws (218, 220) of end effector (214). Closure link (302) transmits closure load via translation of closure tube (304) from distal clevis (300) to proximal clevis (298) such that closure ring (306) correspondingly pushes or pulls on upper jaw (220) to open or close upper jaw (220) relative to lower jaw (218) as applicable.

While the above articulation of end effector (214) relative to longitudinal axis (222) and movement of upper jaw (220) between open and closed positions is shown as described herein, it will be appreciated that such articulation and movement may be performed at end effector (214) with alternative structures. The invention is thus not intended to be unnecessarily limited to the particular end effector (214) with associated wrist (216) and shown and described herein.

B. Activating Mechanisms for Articulation and Jaw Movement i. Articulation Activating Mechanism with Barrel Cam

Figure 9:
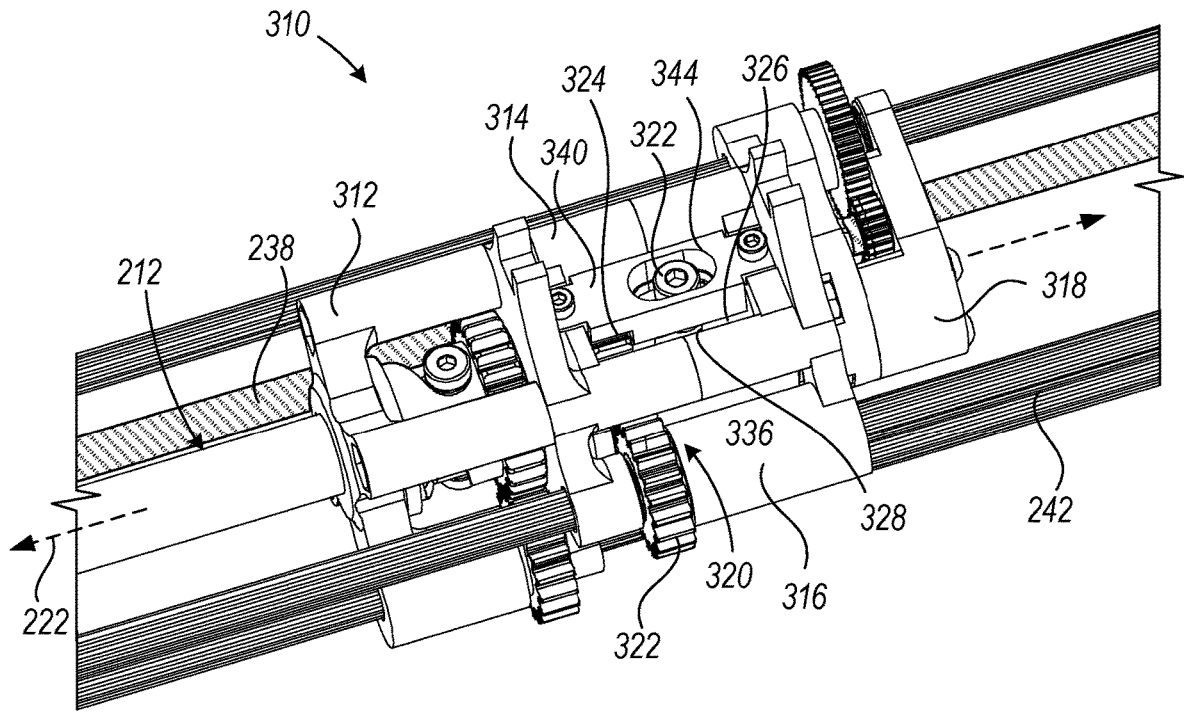
FIG. 9 depicts an enlarged perspective view of a second example of a carriage incorporated into the surgical instrument of FIG. 7 and having an articulation activating mechanism.
Figure 10:
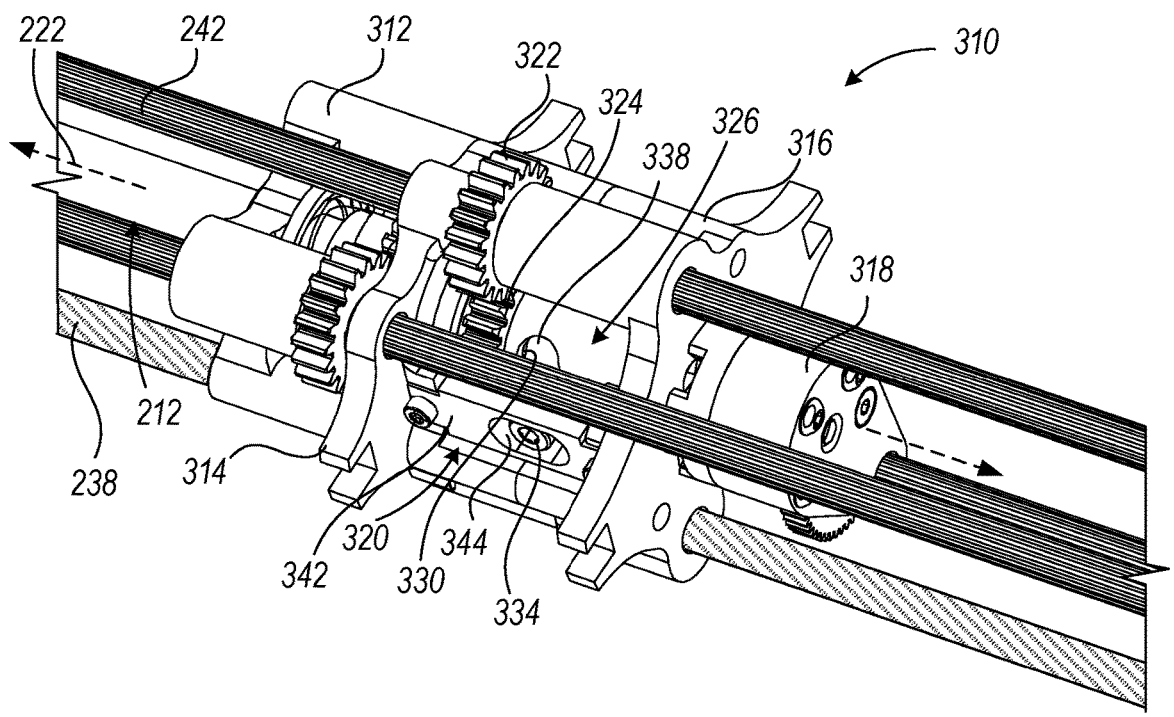
FIG. 10 depicts another enlarged perspective view of the carriage of FIG. 9 incorporated into the surgical instrument of FIG. 7.

FIGS. 9 and 10 show another example of a carriage (310) similar in some respects to carriage (246) (see FIG. 7) discussed above and may replace carriage (246) (see FIG. 7) in one or more examples such that like numbers below indicate like features discussed above. Carriage (310) is thus like carriage (246) (see FIG. 7) unless noted otherwise below. Carriage (310) more particularly has two or more layers, such as a first layer (312), a second layer (314), a third layer (316), and a fourth layer (318). Shaft (212) is coupled to and extends distally from carriage (310) such that carriage (310) is configured to move along longitudinal axis (222) to correspondingly advance or retract end effector (214) shown in FIG. 8A.

With reference to FIGS. 8A and 9-10, carriage (310) includes an activating mechanism (320) configured to articulate end effector (214) relative to longitudinal axis (222) (see FIG. 8A) at wrist (216). Second spline (242) is operatively coupled to activating mechanism (320) such that rotating second spline (242) correspondingly actuates activating mechanism (320) and thereby causes wrist (216) to articulate. More specifically, a drive gear (322) is included with second spline (242) and positioned to intermesh with a driven gear (324) coupled to an articulation barrel (326). As spline (242) rotates, drive gear (322) drives driven gear (324) and correspondingly rotates articulation barrel (326) about longitudinal axis (222).

Articulation barrel (326) of the present example includes a first cam profile (328) and a second cam profile (330). Activating mechanism (320) further includes a first follower pin (332) and a second follower pin (334). First follower pin (332) extends through first cam profile (328) and is coupled to a first carrier (336), and second follower pin (334) extends through second cam profile (330) and is coupled to a second carrier (338). Each cam profile (328, 330) extends about a circumference of articulation barrel (326) (e.g., in a helical pattern), but cam profiles (328, 330) are defined at opposite angles relative to each other. As drive gear (322) drives driven gear (324), articulation barrel (326) correspondingly rotates about longitudinal axis (222), thus urging follower pins (332, 334) to traverse the oppositely-angled cam profiles (328, 330), respectively. As follower pins (332, 334) traverse cam profiles (328, 330), underlying carriers (336, 338) are urged in equal but opposite axial directions along longitudinal axis (222). Depending on a rotational direction of drive gear (322), carriers (336, 338) may be drawn axially toward each other or moved axially away from each other.

In one or more examples, activating mechanism (320) further includes a first articulation torque bar (340) and a second articulation torque bar (342). Articulation torque bars (340, 342) extend between second and third layers (314, 316) and are secured to each layer (314, 316). Each articulation torque bar (340, 342) defines a slot (344) sized to receive heads of corresponding follower pins (332, 334). During use of activating mechanism (320), articulation torque bars (340, 342) are configured to maintain an axial position of corresponding follower pins (332, 334).

Figure 11:
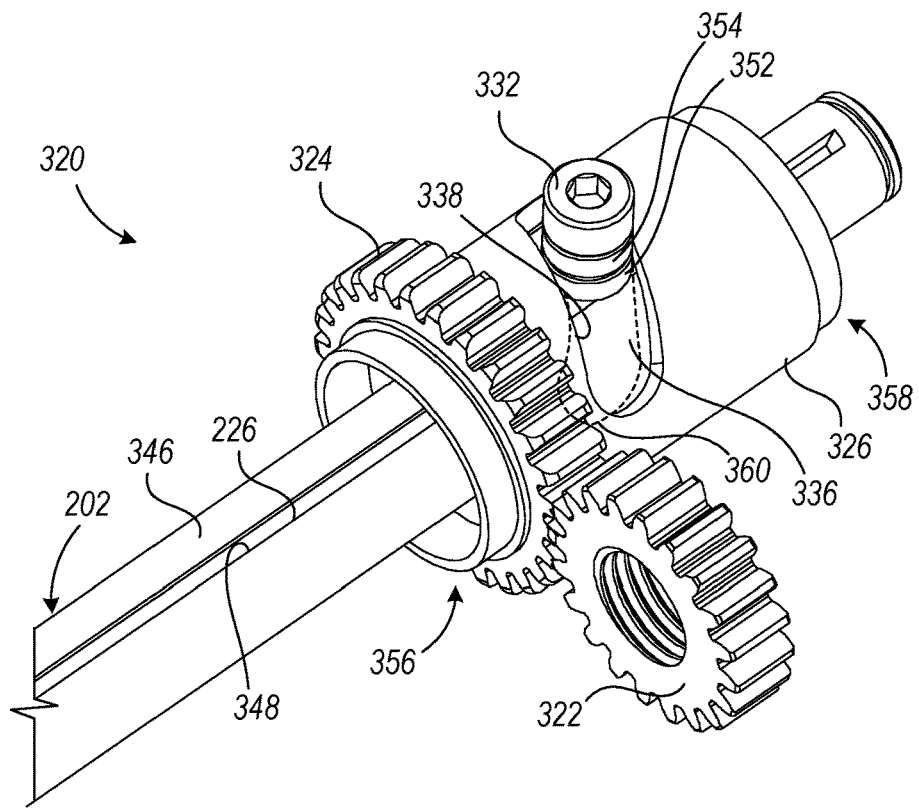
FIG. 11 depicts a perspective view of the articulation activating mechanism of FIG. 9.
Figure 12:
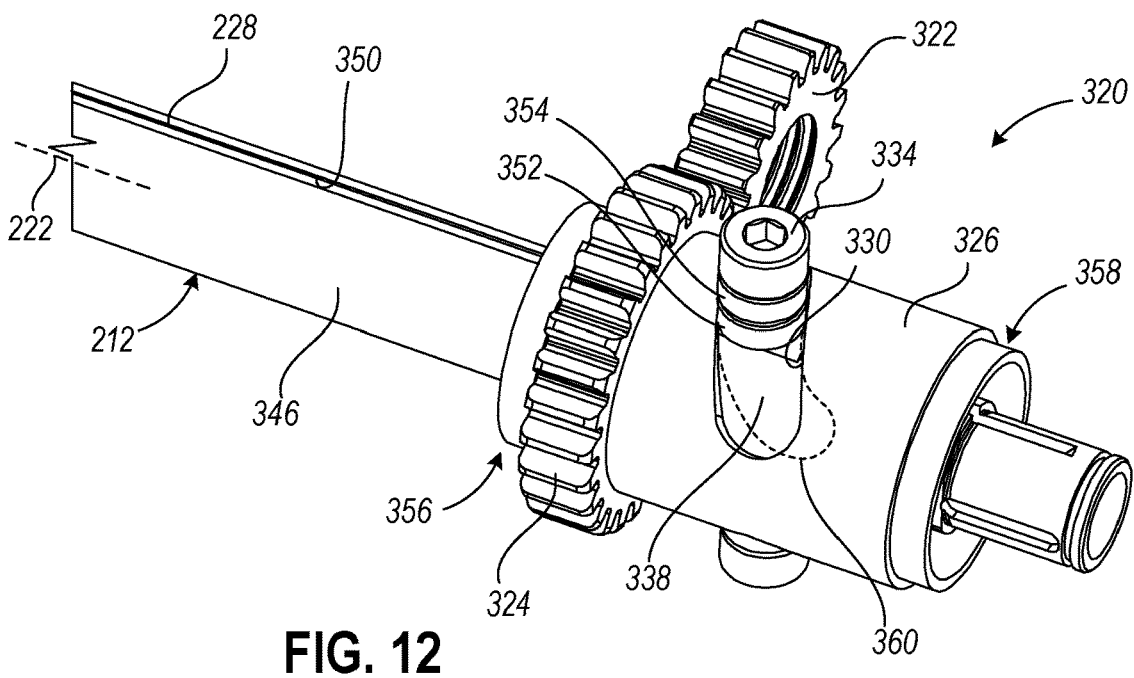
FIG. 12 depicts another perspective view of the articulation activating mechanism of FIG. 9.

FIGS. 11 and 12 more particularly show articulation barrel (326) having a generally cylindrical structure that extends about shaft (212) about an inner grounding shaft (346). First and second carriers (336, 338) interpose inner grounding shaft (346) and articulation barrel (326) and are independently movable along longitudinal axis (222). First carrier (336) is operatively coupled to first drive member (226), which extends distally to wrist (216) (see FIG. 8A) at least partially within a slot (348) defined in inner grounding shaft (346). Additionally, second carrier (338) is operatively coupled to second drive member (228), which extends distally to wrist (216) (see FIG. 8A) at least partially within a slot (350) defined in inner grounding shaft (346).

Follower pins (332, 334) extend through corresponding cam profiles (328, 330) and are coupled to associated carriers (336, 338), respectively. In one example, one or both of follower pins (332, 334) may include bearings, such as a first bearing (352) and a second bearing (354). Such first and second bearings (352, 354) are stacked on top of each other with a shaft of each follower pin (332, 334) extending through first and second bearings (352, 354). First bearings (352) are configured to bear against the inner walls of cam profiles (328, 330) as articulation barrel (326) rotates and follower pins (332, 334) are urged to traverse cam profiles (328, 330) respectively, reducing friction thereagainst. Second bearings (354) are configured to bear against the inner walls of slot (344) (see FIGS. 9-10) defined in corresponding torque articulation bars (340, 342) (see FIGS. 9-10) to prevent rotational movement of follower pins (332, 334) as articulation barrel (326) rotates.

Articulation barrel (326) has a distal end (356) and a proximal end (358), and driven gear (324) may be defined proximate to distal end (356) in one example, provided proximate to proximal end (358) in another example, or alternatively positioned anywhere in between distal and proximal ends (356, 358) in still other examples. Cam profiles (328, 330) are positioned between distal and proximal ends (356, 358) and may comprise straight slots extending at a constant angle about a circumference of articulation barrel (326), but at opposite angular directions. In one example with straight cam profiles (328, 330), movement and force applied to carriers (336, 338) and drive members (226, 228) is constant during articulation of end effector (214) (see FIG. 8A). In such an example, cam profiles (328, 330) may be more particularly described as helical cam slots and follower pins (332, 334) may be more particularly described as linear cam followers.

In another example, cam profiles (328, 330) may not be entirely straight, but may alternatively diverge at one or more inflection points along a length, which may also be referred to as a "path," of cam profile (328, 330). More specifically, cam profiles (328, 330) may diverge from straight and define a more or less aggressive path, such as path (360), depending on a direction at the inflection point. Higher or lower angles of cam profiles (328, 330) alter mechanical advantage obtained as follower pins (332, 334) traverse cam profiles (328, 330) and act on interconnected carriers (336, 338), respectively. Such differing mechanical advantages may be beneficial in one or more uses of articulating end effector (214) relative to longitudinal axis (222).

ii. Jaw Activating Mechanism with Barrel Cam

Figure 13:
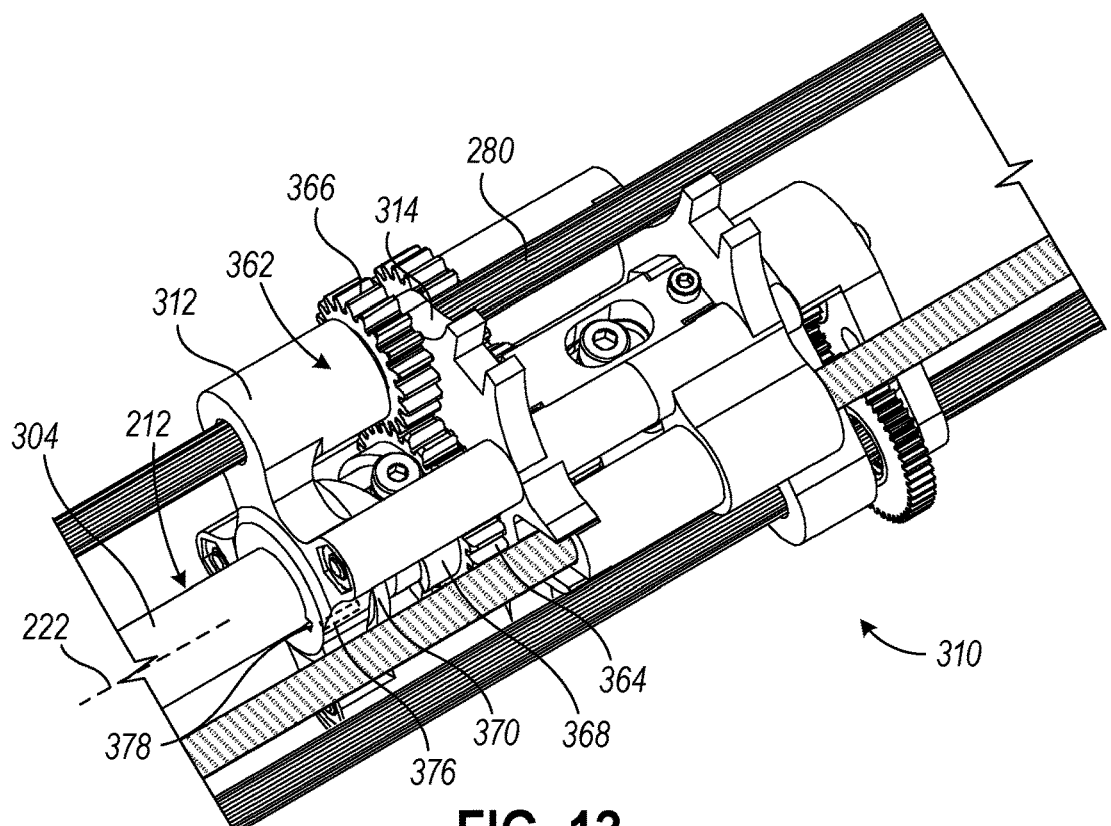
FIG. 13 depicts an enlarged perspective view of the carriage of FIG. 9 having a jaw activating mechanism.
Figure 14:
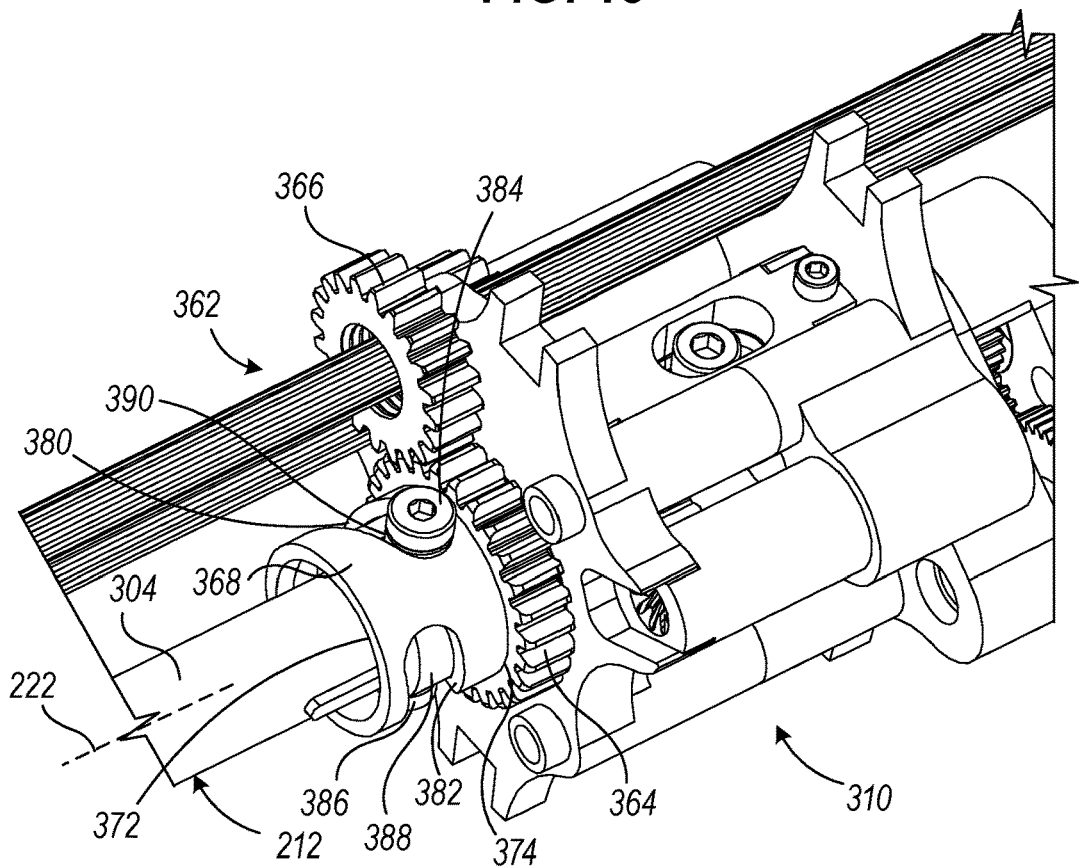
FIG. 14 depicts another enlarged perspective view of the carriage of FIG. 13 with the jaw activating mechanism.

FIGS. 13-14 show carriage (310) discussed above including another activating mechanism (362) configured to move upper jaw (220) relative to lower jaw (218) between the open and closed positions as shown with further reference to FIG. 8B. To this end, first spline (240) is configured to direct such movement of upper jaw (220) such that rotating first spline (240) (e.g., via rotation of second drive input (266) (see FIG. 7) correspondingly actuates activating mechanism (362) and thereby causes closure tube (304) of shaft (212) to advance or retract along longitudinal axis (222).

Activating mechanism (362) further includes a driven gear (364) that intermeshes with a drive gear (366) of first spline (240) such that rotation of drive gear (366) correspondingly rotates driven gear (364). As shown in the present example, driven gear (364) is coupled with a closure barrel (368). As spline (240) rotates, drive gear (366) drives driven gear (364) and causes closure barrel (368) to rotate about longitudinal axis (222). Closure barrel (368) is positioned in carriage (310) between first and second layers (312, 314). One or more thrust bearings may be arranged at one or both axial ends of closure barrel (368) to effectively bear axial loading on closure barrel (368) and reduce friction during use of activating mechanism (362). More particularly, a plurality of thrust bearings (370) in the present example is arranged at a distal end (372) of closure barrel (368), which is opposite from a proximal end (374) of closure barrel (368) and interpose closure barrel (368) and first layer (248). Additionally, activating mechanism (362) further includes a key (376) on the outer surface of closure tube (304). Key (376) is received within a slot (378) defined in first layer (312) of carriage (310). Actuating activating mechanism (362) causes closure tube (304) to translate along longitudinal axis (222) and correspondingly causes key (376) to translate longitudinally within slot (378) to thereby prevent closure tube (304) from rotating during longitudinal movement of closure tube (304).

Closure barrel (368) has a generally cylindrical structure that extends about closure tube (304) and defines a first cam profile (380) and a second cam profile (382). Each cam profile (380, 382) extends a distance about a circumference of closure barrel (368) (e.g., in a generally helical pattern). While closure barrel (368) provides two cam profiles (380, 382) the invention is not intended to be unnecessarily limited to two such cam profiles (380, 382) such that an alternative number of cam profiles may be similarly incorporated into closure barrel (368).

Activating mechanism (362) further includes a first follower pin (384) and a second follower pin (386) extending through first and second cam profiles (380, 382), respectively, and are operatively coupled to a proximal end of closure tube (304). In one example, first and second follower pins (384, 386) are each coupled to a carrier (388) arranged at the proximal end of closure tube (304). Carrier (388) is configured to receive the proximal end of closure tube (304) and may radially interpose a portion of closure tube (304) and closure barrel (368), and movement of carrier (388) along longitudinal axis (222) will correspondingly move closure tube (304) in a like axial direction.

As drive gear (366) drives driven gear (364), closure barrel (368) correspondingly rotates about longitudinal axis (222), thus urging follower pins (384, 386) to traverse cam profiles (380, 382), respectively. In turn, carrier (388) moves along longitudinal axis (222), and closure tube (304) is urged in the same axial direction. Depending on the rotational direction of drive gear (366), carrier (388) and closure tube (304) may move distally (i.e., to the left in FIG. 14) or proximally (i.e., to the right in FIG. 14) and thereby close or open jaws (218, 220) of end effector (214) as shown in FIG. 8B.

In one example, one or both of follower pins (384, 386) may include one or more bearings (390), and shaft of each follower pin (384, 386) extends through bearings (390). Bearings (390) are configured to bear against inner walls of cam profiles (380, 382) as closure barrel (368) rotates and follower pins (384, 386) traverse cam profiles (380, 382) thereby reducing friction during use.

Figure 15:
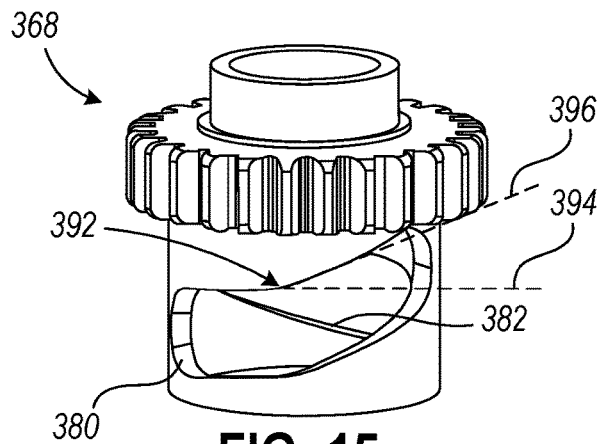
FIG. 15 depicts a first exemplary barrel cam of the jaw activating mechanism of FIG. 13.

FIG. 15 shows one example of the closure barrel (368) in greater detail. As discussed briefly above, each cam profile (380, 382) has a slot extending generally helically about a portion of the circumference of closure barrel (368). In such an example, cam profiles (380, 382) may be more particularly described as helical cam slots, and follower pins (384, 386) may be more particularly described as linear cam followers. Each cam profile (380, 382) has a straight slot extending helically at a constant angle, which may also be referred to herein as a slope, about the circumference of closure barrel (368). The movement applied to carrier (388) and converted into an axial load on closure tube (304) (see FIGS. 13-14) may be constant during actuation of activating mechanism (362) (FIGS. 13-14) through this constant angle.

In one example, one or both of cam profiles (380, 382) may not be entirely straight, but may alternatively diverge at one or more inflection points (392) along a helical length of cam profile (380, 382). More specifically, at inflection point (392), cam profiles (380, 382) change from extending a first distance about the circumference of closure barrel (368) at a first slope (394) to a second distance at a second slope (396) such that second slope (396) has a more or less aggressive path as compared to first slope (394). A higher or lower slope of cam profile (380, 382) will correspondingly alter a mechanical advantage obtained as follower pins (384, 386) traverse cam profiles (380, 382) and act on interconnected carrier (388). Such mechanical advantage may result in higher axial loads being applied to closure tube (304) (see FIGS. 13-14) and allow jaws (218, 220) (see FIG. 8B) to clamp down with enhanced force and/or greater precision during use.

III. Carrier with Translatable Activating Mechanisms

While activating mechanisms (272, 274, 276, 320, 362) are configured to transmit movement from robotically driven inputs to one or more various portions of surgical instrument (210), each may be functionally locked together during use as discussed above. In this respect, any attempt to manually move outputs associated with these one or more various portions of surgical instrument (210), such as jaws (218, 220), generally would require movement of respective activating mechanisms (272, 274, 276, 320, 362) and even the associated robotically driven input. In some instances though, it may be desirable to enable the operator to access and manually manipulate one or more of activating mechanisms (272, 274, 276, 320, 362) directly to move the outputs associated with these one or more various portions of surgical instrument (210) without affecting movement of the robotically driven inputs. For example, in the event that debris, such as tissue, becomes lodged between jaws (218, 220) during use, the operator may desire to effectively "bailout" of the robotically driven actuation and opt to manually move jaws (218, 220) to clear the debris. Such a configuration may reduce downtime and improve resumption of ordinary use of robotic direction of surgical instrument (210).

Figure 16:
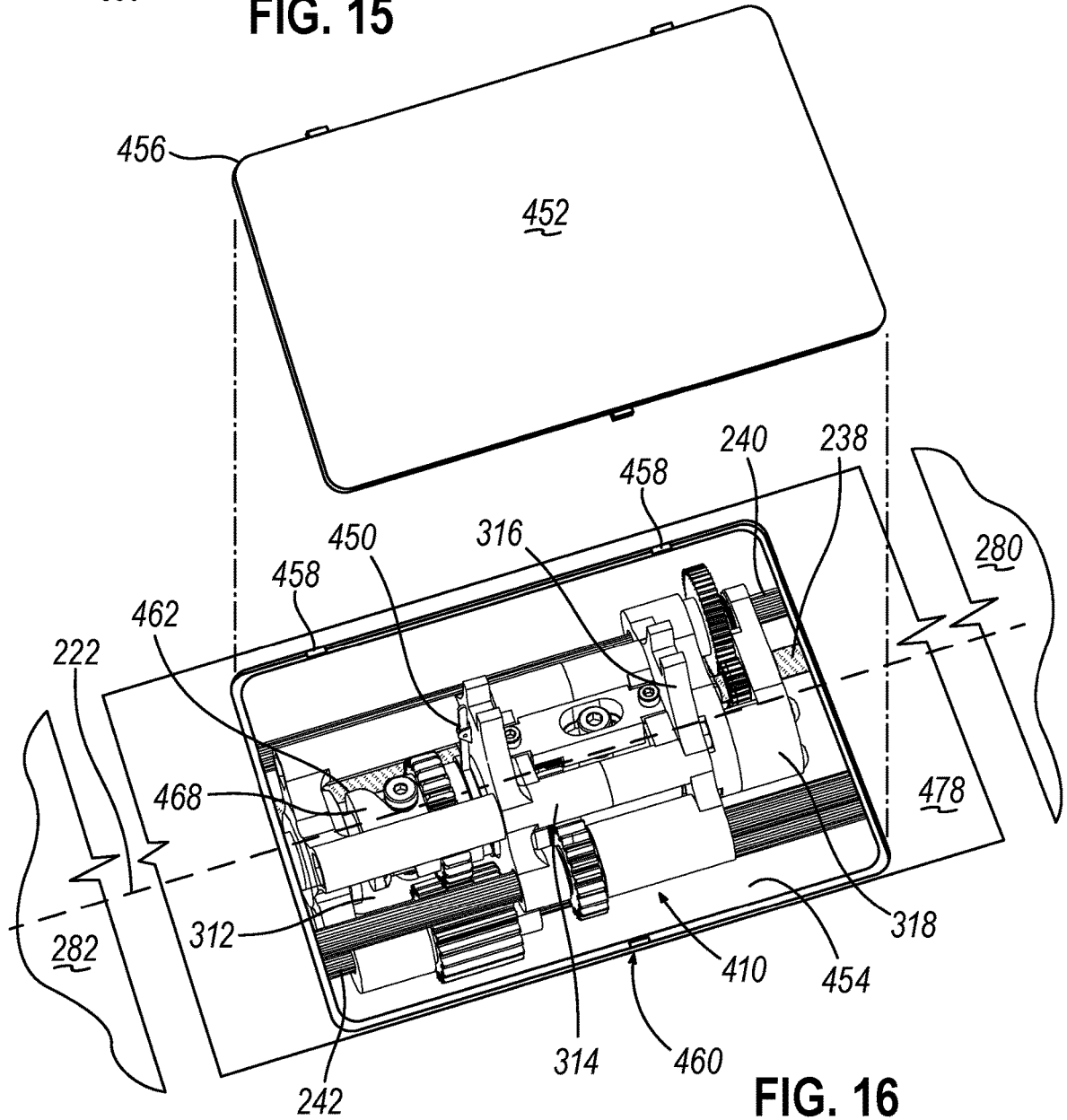
FIG. 16 depicts an enlarged perspective view of a third example of a carriage with another example of a jaw activating mechanism viewed through an opening.

FIG. 16 shows yet another example of a carriage (410) and a shroud (478) similar in some respects to carriage (310) (see FIG. 13-14) and shroud (278) (see FIG. 7) discussed above and may respectively replace carriage (310) (see FIG. 13-14) and shroud (278) (see FIG. 7) in one or more examples such that like numbers below indicate like features discussed above. In this respect, carriage (410) is like carriage (310) (see FIG. 13-14) and shroud (478) is like shroud (278) (see FIG. 7) unless noted otherwise below.

Activating mechanism (462) is driven by a rotational driver (440) and includes an actuation body (468) similar to closure barrel (368) of activating mechanism (362). In one example, actuation body (468) is singularly and unitarily formed, but, in another example, actuation body (468) is formed as an assembly. Actuation body (468) is thus not intended to be unnecessarily limited to any particular construction. Actuation body (468) is configured to be rotated by rotational driver (440) from a first rotational body position towards a second rotational body position to selectively direct closure tube (304) to act upon end effector (214) (see FIG. 8A), such as to direct movement of jaws (218, 220).

In addition to rotational driver (440), and unlike activating mechanism (362), activating mechanism (462) is also configured to be driven by a translational driver (450) to translate actuation body (468) of activating mechanism (462) relative to longitudinal axis (222) from a first translational body position towards a second translational body position. In turn, activating mechanism (462) selectively directs closure tube (304) to act as a drive member upon end effector (214) (see FIG. 8A). Carriage (410) like carriage (310) includes two or more layers, such as first layer (312), second layer (314), third layer (316), and fourth layer (318) although carriage (410) differs from carriage (310) in that first layer (312) is spaced farther apart from second layer (314) to provide additional space for translational driver (450) to translate actuation body (468) along longitudinal axis (222).

Shroud (478) is similar in some respects to shroud (278) in that shroud (478) is sized to receive and otherwise surround carriage (410), lead screw (238), and splines (240, 242, 244). Shroud (478) differs from Shroud (278) in that Shroud (478) further includes an access assembly (452) configured to enable the operator to inspect carriage (410) and manipulate translational driver (450). To this end, access assembly (452) includes an opening (454), an access cover (456), at least one or more tabs (458), and at least one or more fasteners (460). Access assembly (452) may be located at proximal end (282) (see FIG. 7) of shroud (478), distal end (280) (see FIG. 7) of shroud (478), or anywhere between proximal and distal ends (282, 280) (see FIG. 7). In other versions, an alternative access assembly may additionally or alternatively include a longitudinal slot (not shown) that runs a full length of shroud (478) from proximal end (282) to distal end (280) so that carriage (410) may be accessed at any position within shroud (478).

Opening (454) is defined by a recessed portion of shroud (478). Access cover (456) is sized to fit over and cover opening (454). In the present version, access cover (456) includes a hard material such as plastic, stainless steel, or aluminum. In other versions, access cover (456) cover is constructed of a resilient material such as silicone or rubber that is compressed to within opening (454) without any tabs (458) or fasteners (460). In the present version, tabs (458) block access cover (456) from being tangentially inadvertently removed from opening (454) and provide friction to retain access cover (456) during use. Although it will be appreciated that any securement, such as an additional latch (460), including fasteners, may be similarly used for removably retaining access cover (456) over opening (454). In yet further versions, carriage (410) is accessed by removing another portion shroud (478), or even an entirety of shroud (478) from drive housing (224).

Figure 17:
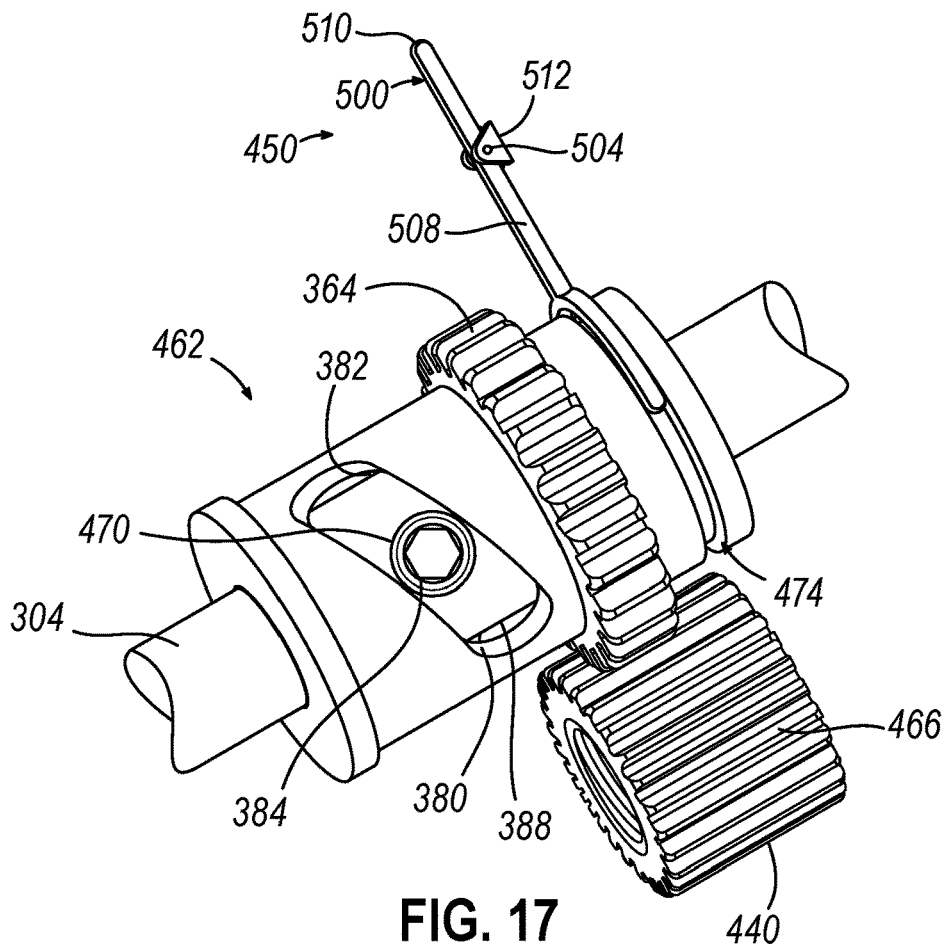
FIG. 17 depicts an enlarged perspective view of the activating mechanism of FIG. 16 in an intermediate body position.

FIG. 17 shows activating mechanism (462) in an intermediate body position mated with both rotational driver (440) and translational driver (450). Activating mechanism (462) includes actuation body (468), a driven gear (364), and an annular channel (474). The intermediate body position is between first and second rotational body positions and between first and second translational positions (see FIG. 20A and FIG. 20B). Activating mechanism (462) is intermeshed with rotational driver (440) and is slidably coupled to translational driver (450). Driven gear (364) intermeshes with a drive gear (466) of translational driver (450). Drive gear (466) of activating mechanism (362) is wider than drive gear (366) discussed above to facilitate intermeshing with driven gear (364) and accommodate travel from the first translational body position to the second translational body position.

Activating mechanism (462) further includes a first follower (470) having follower pins (384, 386) extending transversely through first and second cam profiles (380, 382), respectively. Follower pins (384, 386) are operatively coupled to closure tube (304) via carrier (388). Carrier (388) is configured to receive proximal end of closure tube (304) and may radially interpose a portion of closure tube (304) and actuation body (468). Movement of carrier (388) along longitudinal axis (222) will correspondingly move closure tube (304) in the same axial direction. Closure tube (304) is coupled to and extends distally from carrier (388) such that carriage (410) is configured to move upper jaw (220) (see FIG. 8B) relative to lower jaw (218) (see FIG. 8B) between the open and closed positions.

Figure 18:
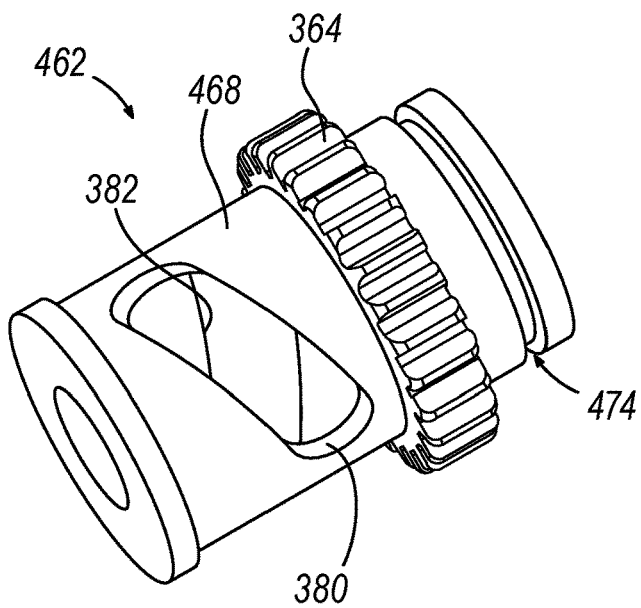
FIG. 18 depicts an enlarged perspective view of an actuation body of the activating mechanism of FIG. 17.

FIG. 18 shows actuation body (468) in greater detail. In the present version, actuation body (468) is cylindrically shaped, although actuation body (468) may include any shape such as a square, a rectangular, an oval, or any other tubular shape that may be rotatably coupled around closure tube (304) (see FIG. 17). Actuation body (468) is similar to closure barrel (368) and defines cam profiles (380, 382), each having a slot extending generally helically about a portion of the circumference of actuation body (468). In the present version, there are two cam profiles (380, 382) so that the axial load on closure tube (304) and/or shaft (212) is balanced. However, additional cam profiles or only one cam profile may be defined by actuation body (468). Actuation body (468) may include bearings (not shown), or bushings (not shown) fitted around closure tube (304) to facilitate rotational and translational movement relative to closure tube (304).

Actuation body (468) differs from closure barrel (368) in that actuation body (468) further includes an annular channel (474) that encircles the circumference of actuation body (468). Annular channel (474) is configured to receive translational driver (450) such that the annular shape of annular channel (474) allows translational driver (450) longitudinally engage actuation body (468) without functionally affecting rotation of actuation body (468). In other versions, actuation body (468) may additionally or alternatively include recessed channels, holes, or any surface suitable to transmit linear force from translation driver (450) to actuation body (468). In some versions, a thrust washer (not shown) may be added to annular channel (474) to transmit axial loading by rotational driver (440) (see FIG. 17) and translational driver (450) (see FIG. 17). In any case, the invention is not intended to be unnecessarily limited to the particular annular channel (474) and translational driver (450) shown in the present example.

Figure 19:
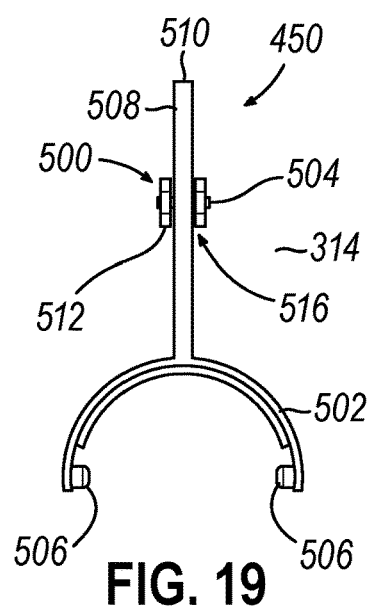
FIG. 19 depicts a side elevational view of a translational driver of the jaw activating mechanism of FIG. 16 for use with the actuation body of FIG. 18.

With respect to FIG. 19, translational driver (450) includes a yoke (502), a translation arm (500), and a fulcrum (504) for coupling with and selectively directing translation of actuation body (468). To this end, yoke (502) has an arcuate shape that extends 180 degrees within annular channel (474). In other versions, yoke (502) may extend up to 360 degrees around annular channel (474). In yet other versions, yoke (502) engages a proximal end of actuation body (468), a distal end of actuation body (468), both a proximal and distal end of actuation body (468) or may only have a single point of contact with actuation body (468). In the present version, yoke (502) includes two yoke pins (506) positioned transverse to longitudinal axis (222) within annular channel (474). However, any number of yoke pins (506) may be used to engage actuation body (468). In yet further versions, yoke (502) may include an annular ring (not shown) positioned within annular channel (474) of actuation body (468).

Translation arm (500) includes a lever (508) that extends transversely away from yoke (502), towards a lever end (510) and extends through fulcrum (504). Fulcrum (504) includes a base (512) and a pivot pin (514). In the present version, base (512) is secured to second layer (314) (see FIG. 16) but may be secured to any rigid portion of carriage (410) (see FIG. 16) so long as it is fixed relative to carriage (410) (see FIG. 16). Base (512) is spaced apart from second layer (314) (see FIG. 16) to allow lever (508) to move about pivot pin (514). Lever (508) is rotatably coupled to base (512) by pivot pin (514). Pivot pin (514) enables the operator to rotate lever (508) about base (512). Fulcrum (504) provides mechanical advantage to translate actuation body (468). Additionally or alternatively, mechanical advantage may be obtained by gears or pulleys. Lever (508) rotates lever about fulcrum (504) in the opposite direction that the operator desires to move actuation body (468). In other versions, translation arm (500) may be otherwise supported and translate in the direction the operator desires to move actuation body (468). One such structure would be a bearing surface (not shown) and/or a race (not shown).

In some versions, translation arm (500) includes a lockout mechanism (516) Lockout mechanism (516) is capable of transitioning lever (508) from a locked state to an unlocked state and vice versa. Lockout mechanism (516) may include a switch, a button, or other actuation device known to those of ordinary skill in the art to inhibit movement. In the locked state, lockout mechanism (516) prevents translation arm (500) from rotating about fulcrum (504) such that actuation body (468) does not translate in the locked state. The operator transitions lockout mechanism (516) between the unlocked state and the locked state by depressing lockout mechanism (516) with a finger or otherwise acting upon lockout mechanism (516). In other versions, lockout mechanism (516) may include a resilient member (not shown) configured to return lockout mechanism (516) to the unlocked state when lockout mechanism (516) is released by the operator. In yet other versions, lockout mechanism (516) stays in the locked state until the operator acts upon lockout mechanism (516) to transition lockout mechanism (516) from the locked state to the unlocked state. In the locked state, translation arm (500) enables rotational driver (440) to selectively rotate actuation body (468) from the first rotational body position to the second rotational body position while inhibiting translation.

Figure 20A:
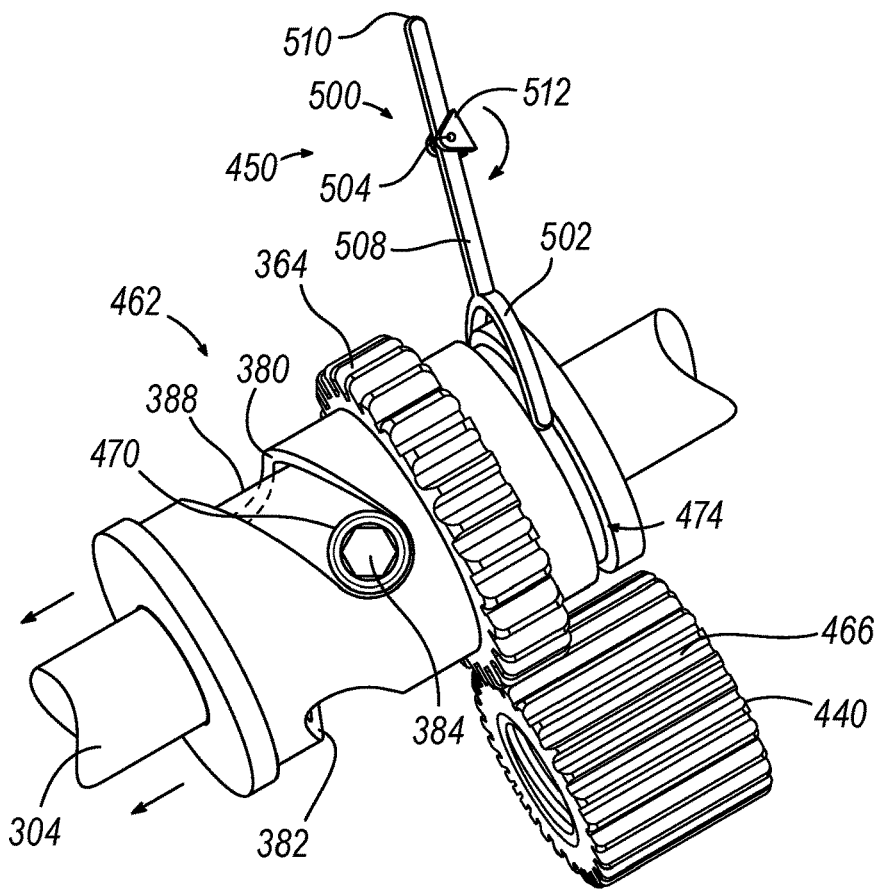
FIG. 20A depicts an enlarged perspective view of the activating mechanism of FIG. 17 in a first translational body position.

FIG. 20A shows translational driver (450) transitioning actuation body (468) distally from the intermediate body position (see FIG. 17) to the first translational body position. Lever end (510) proximally rotates about fulcrum (504) moving yoke (502) distally. Yoke pins (506) engage annular channel (474) and translate annular channel (474) distally. The distal movement of actuation body (468) moves cam profiles (380, 382) distally until follower pins (384, 386) reach a proximal most portion of cam profiles (380, 382). Proximal most portion of cam profiles (380, 382) engage follower pins (384, 386) and translate follower pins (384, 386) distally. Follower pins (384, 386) are coupled to and translate carrier (388) distally. Carrier (388) is coupled to and translate closure tube (304) distally. Closure tube (304) is coupled to and acts upon one of jaws (218, 220) (see FIG. 8B) to close jaws (218, 220) (see FIG. 8B) of end effector (214) (see FIG. 8B).

Figure 20B:
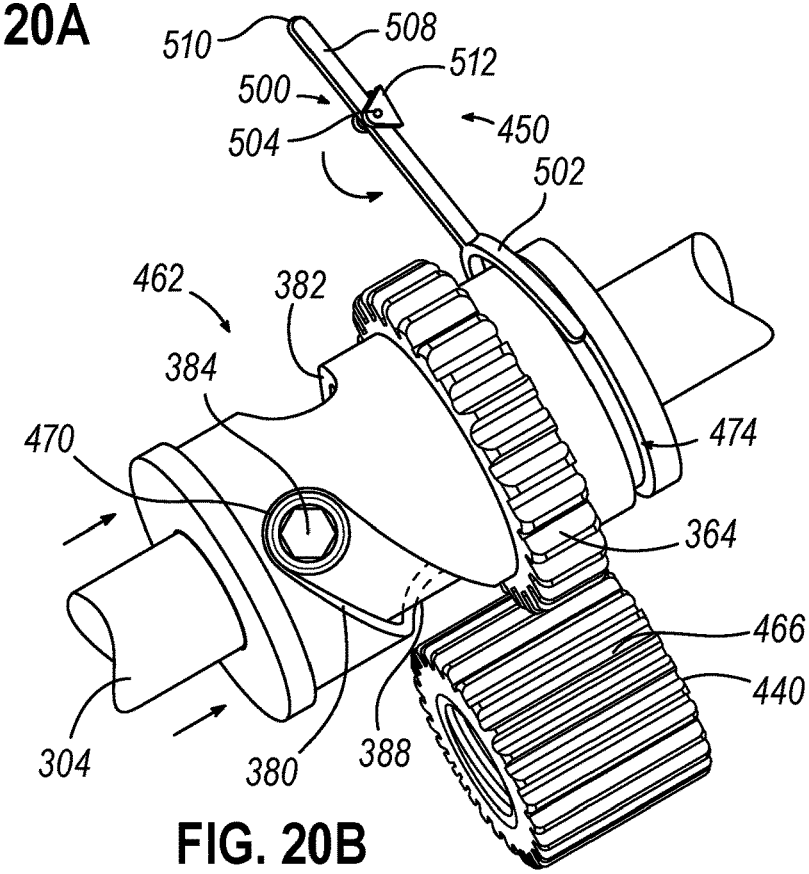
FIG. 20B depicts the enlarged perspective view of the activating mechanism similar to FIG. 20A, but with the activating mechanism in a second translational body position.

FIG. 20B shows translational driver (450) transitioning actuation body (468) proximally from the first translational body position (see FIG. 17) to the second translational body position, such as in the event of a manual bailout for opening jaws (218, 220). Lever end (510) distally rotates about fulcrum (504) moving yoke (502) proximally. Yoke pins (506) engage annular channel (474) and translate annular channel (474) proximally. The distal movement of actuation body (468) moves cam profiles (380, 382) proximally until follower pins (384, 386) reach a distal most portion of cam profiles (380, 382). Distal most portion of cam profiles (380, 382) engage follower pins (384, 386) and translate follower pins (384, 386) proximally. Follower pins (384, 386) are coupled to and translate carrier (388) proximally. Carrier (388) is coupled to and translate closure tube (304) proximally. Closure tube (304) is coupled to and acts upon one of jaws (218, 220) (see FIG. 8B) to open jaws (218, 220) (see FIG. 8B) of end effector (214) (see FIG. 8B), such as for clearing debris from jaws (218, 220) (see FIG. 8B).

Figure 21:
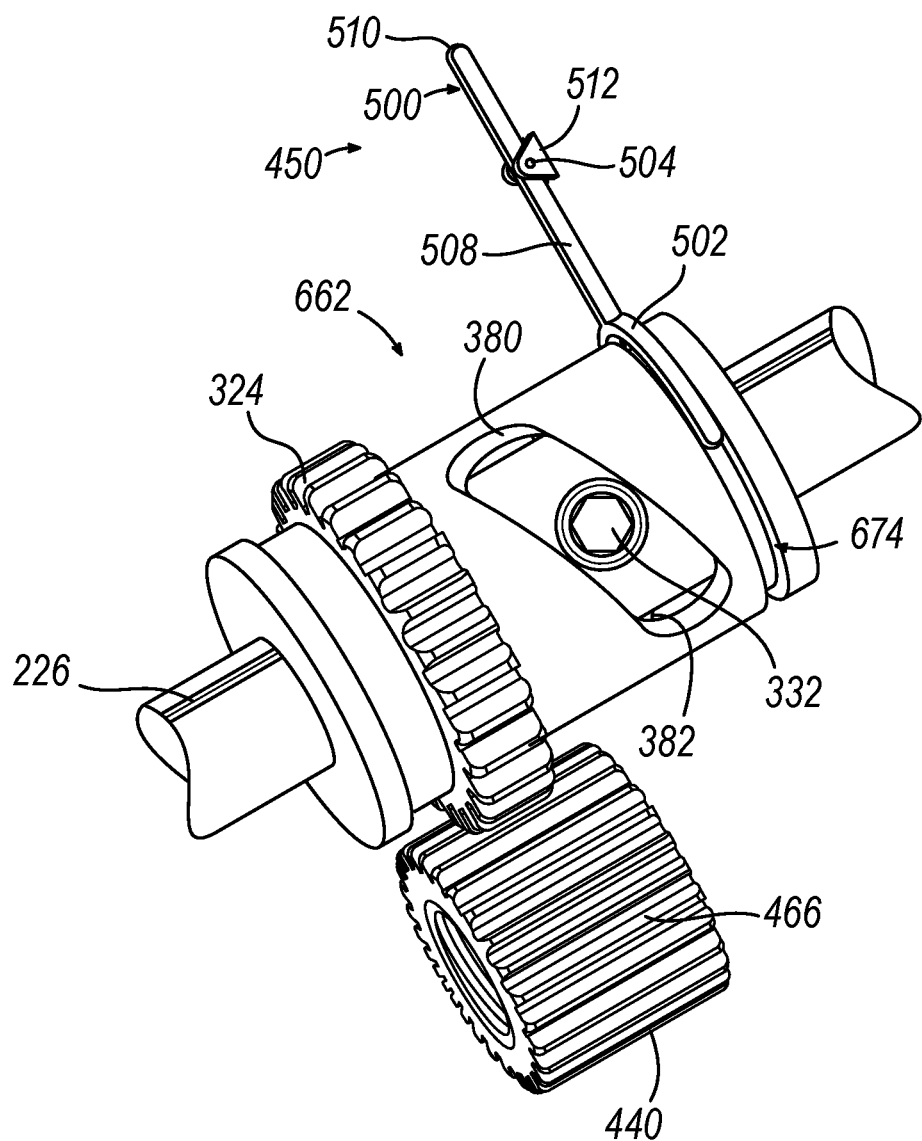
FIG. 21 depicts an enlarged perspective view of a second example of an articulation activating mechanism with a translational driver.

FIG. 21 shows yet another activating mechanism (662) mated with a rotational driver (440) and a translational driver (450). Activating mechanism (662) is similar in some respect to activating mechanism (320) in that activating mechanism (662) is actuated by rotational driver (440) to articulate end effector (214) (see FIG. 8A) relative to longitudinal axis (222) (see FIG. 8A). Activating mechanism (662) is unlike activating mechanism (320) in that activating mechanism (662) has annular channel (674), which is similar to annular channel (474) discussed above, mated with translational driver (450) for similarly performing a manual bailout associated with articulation of end effector (214) (see FIG. 8A). Activating mechanism (662) includes like features to activating mechanism (320) discussed above indicated by like numbers below.

Activating mechanism (662) is configured to be incorporated into carriage (not shown) similar to carriage (410) (see FIG. 16). Carriage (not shown) includes a second layer (314) (see FIG. 16) spaced farther from third layer (316) (see FIG. 16) to accommodate the axial movement of activating mechanism (662). In operation, translational driver (450) actuates activating mechanism (662) to articulate end effector (214) (see FIG. 8A) relative to longitudinal axis (222) (see FIG. 8A) at wrist (216) (see FIG. 8A).

More specifically, lever end (510) may be proximally or distally rotated about fulcrum (504) thereby moving yoke (502) distally and proximally respectively. Yoke (502) translates annular channel (674) of actuation body (668) about longitudinal axis (222) in the same axial direction as yoke (502). First and second cam profiles (328, 330) (see FIGS. 9-10) translate first and second follower pins (332, 334) (see FIGS. 9-10) thereby translating first and second carriers (336, 338) (see FIGS. 9-10) proximally or distally from an intermediate body position towards a first translational body position or a second translational body position. First and second carriers (336, 338) (see FIGS. 9-10) translate first and second drive members (226, 228) (see FIG. 8A), which extend distally on opposite sides of wrist (216), (see FIG. 8A) to correspondingly rotate end effector (214) (see FIG.

8A) in first direction and second direction transverse to longitudinal axis (222). It will thus be appreciated that such structures for manual bailout may be incorporated into any robotically driven features such that bailout functionality is not intended to be unnecessarily limited to movement of jaws (218, 220) (see FIG. 8B) or articulation of end effector (214) (see FIG. 8A).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector; (b) a shaft assembly extending proximally from the end effector, wherein the shaft assembly defines a longitudinal axis; (c) a first drive operatively connected to a first portion of at least one of the end effector or the shaft assembly, wherein the first drive is configured to longitudinally translate relative to the longitudinal axis from a first drive position toward a second drive position to respectively actuate the first portion from a first portion position toward a second portion position; and (d) an activating mechanism including an actuation body operatively connected to the first drive and configured to rotate from a first rotational body position toward a second rotational body position to selectively direct translation of the first drive from the first drive position toward the second drive position, and wherein the actuation body is further configured to translate relative to the longitudinal axis from a first translational body position toward a second translational body position to selectively direct translation of the first drive from the first drive position toward the second drive position.

Example 2

The surgical instrument of Example 1, wherein the end effector includes a jaw, and wherein the first portion of at least one of the end effector or the shaft assembly includes the jaw of the end effector.

Example 3

The surgical instrument of Example 2, wherein the end effector is configured to staple a tissue of a patient.

Example 4

The surgical instrument of Example 3, wherein the jaw includes an anvil configured to deform a plurality of staples.

Example 5

The surgical instrument of Example 1, wherein the shaft assembly includes an articulation section, and wherein the first portion of at least one of the end effector or the shaft assembly includes the articulation section of the shaft assembly.

Example 6

The surgical instrument of Example 1, wherein the first drive includes a first follower, wherein the actuation body includes a cam slot, and wherein the first follower is received within the cam slot such that the cam slot guides movement of the first follower from the first drive position toward the second drive position as the actuation body rotates from the first rotational body position toward the second rotational body position.

Example 7

The surgical instrument of Example 6, wherein the first follower is received within the cam slot such that the cam slot guides movement of the first follower from the first drive position toward the second drive position as the actuation body translates from the first translational body position toward the second translational body position.

Example 8

The surgical instrument of Example 7, wherein the actuation body is a barrel cam having the cam slot, wherein the barrel cam is positioned on the longitudinal axis and configured to selectively rotate about the longitudinal axis, and wherein the barrel cam is further configured to selectively translate along the longitudinal axis.

Example 9

The surgical instrument of Example 1, wherein the actuation body is configured to be rotationally locked relative to the longitudinal axis as the actuation body translates relative to the longitudinal axis.

Example 10

The surgical instrument of Example 1, wherein the actuation body is configured to be translationally locked relative to the longitudinal axis as the actuation body rotates relative to the longitudinal axis.

Example 11

The surgical instrument of Example 1, wherein the activating mechanism further includes a rotational driver and a translational driver, wherein the rotational driver is engaged with the actuation body and configured to selectively rotate the actuation body from the first rotational body position toward the second rotational body position, and wherein the translational driver is engaged with the actuation body and configured to selectively translate the actuation body from the first translational body position toward the second translational body position.

Example 12

The surgical instrument of Example 11, wherein the rotational driver includes a drive gear and the actuation body includes a driven gear, wherein the first translational body position is a proximal-most position and the second translational body position is a distal-most position, and wherein the drive gear remains engaged with the driven gear in each of the proximal-most position and the distal-most position.

Example 13

The surgical instrument of Example 11, wherein the translational driver includes a yoke engaged with the actuation body, and wherein the yoke remains engaged with the actuation body while rotating the actuation body.

Example 14

The surgical instrument of Example 13, wherein the yoke includes a pin and the actuation body includes an annular channel, and wherein the pin is movably received within the annular channel such that the pin remains engaged with the actuation body while rotating the actuation body.

Example 15

The surgical instrument of Example 13, wherein the translational driver includes a lever pivotally secured relative to the actuation body and configured to be selectively manipulated from a first lever position toward a second lever position thereby urging the actuation body from the first translational body position toward the second translational body position.

Example 16

A surgical instrument, comprising: (a) an end effector having a first jaw movably secured relative to a second jaw, wherein the first jaw is configured to move from a closed position toward an opened position; (b) a shaft assembly extending proximally from the end effector, wherein the shaft assembly defines a longitudinal axis; (c) a first drive including a first follower and operatively connected to the first jaw, wherein the first drive is configured to longitudinally translate relative to the longitudinal axis from a first drive position toward a second drive position to respectively actuate the first jaw from the closed position toward the opened position; and (d) an activating mechanism including an actuation body configured to rotate from a first rotational body position toward a second rotational body position, wherein the actuation body has a cam slot, wherein the first follower is received within the cam slot such that the cam slot guides movement of the first follower from the first drive position toward the second drive position as the actuation body rotates from the first rotational body position toward the second rotational body position, wherein the actuation body is further configured to translate relative to the longitudinal axis from a first translational body position toward a second translational body position such that the cam slot guides movement of the first follower from the first drive position toward the second drive position as the actuation body translates from the first translational body position toward the second translational body position, wherein the actuation body is configured to be rotationally locked relative to the longitudinal axis as the actuation body translates relative to the longitudinal axis, and wherein the actuation body is configured to be translationally locked relative to the longitudinal axis as the actuation body rotates relative to the longitudinal axis.

Example 17

The surgical instrument of Example 16, wherein the activating mechanism further includes a rotational driver and a translational driver, wherein the rotational driver is engaged with the actuation body and configured to selectively rotate the actuation body from the first rotational body position toward the second rotational body position, and wherein the translational driver is engaged with the actuation body and configured to selectively translate the actuation body from the first translational body position toward the second translational body position.

Example 18

The surgical instrument of Example 17, wherein the rotational driver includes a drive gear and the actuation body includes a driven gear, wherein the first translational body position is a proximal-most position and the second translational body position is a distal-most position, and wherein the drive gear remains engaged with the driven gear in each of the proximal-most position and the distal-most position.

Example 19

The surgical instrument of Example 18, wherein the translational driver includes a yoke engaged with the actuation body, wherein the yoke remains engaged with the actuation body while rotating the actuation body, wherein the yoke includes a pin and the actuation body includes an annular channel, and wherein the pin is movably received within the annular channel such that the pin remains engaged with the actuation body while rotating the actuation body.

Example 20

A method of actuating a first portion of at least one of an end effector or a shaft assembly of a surgical instrument, wherein the surgical instrument includes (a) the end effector; (b) the shaft assembly extending proximally from the end effector, wherein the shaft assembly defines a longitudinal axis; (c) a first drive operatively connected to the first portion of at least one of the end effector or the shaft assembly, wherein the first drive is configured to longitudinally translate relative to the longitudinal axis from a first drive position toward a second drive position to respectively actuate the first portion from a first portion position toward a second portion position; and (d) an activating mechanism including an actuation body operatively connected to the first drive and configured to rotate from a first rotational body position toward a second rotational body position to selectively direct translation of the first drive from the first drive position toward the second drive position, and wherein the actuation body is further configured to translate relative to the longitudinal axis from a first translational body position toward a second translational body position to selectively direct translation of the first drive from the first drive position toward the second drive position, the method comprising: (a) translating the actuation body while simultaneously inhibiting rotation of the actuation body to direct translation of the first drive from the first drive position toward the second drive position thereby actuating the first portion from the first portion position toward the second portion position.

Example 21

A robotic surgical system, comprising: (a) a robotic arm and (b) A surgical instrument operatively attached to the robotic arm, comprising: (i) an end effector; (ii) a shaft assembly extending proximally from the end effector, wherein the shaft assembly defines a longitudinal axis; (iii) a first drive operatively connected to a first portion of at least one of the end effector or the shaft assembly, wherein the first drive is configured to longitudinally translate relative to the longitudinal axis from a first drive position toward a second drive position to respectively actuate the first portion from a first portion position toward a second portion position; and (iv) an activating mechanism including an actuation body operatively connected to the first drive and configured to rotate from a first rotational body position toward a second rotational body position to selectively direct translation of the first drive from the first drive position toward the second drive position, and wherein the actuation body is further configured to translate relative to the longitudinal axis from a first translational body position toward a second translational body position to selectively direct translation of the first drive from the first drive position toward the second drive position.

V. Miscellaneous

Any one or more of the teaching, expressions, embodiments, examples, etc. described herein may be combined with any one or more of the teachings, expressions, embodiments, examples, etc. described in U.S. patent application Ser. No. 17/245,332, entitled "Variable Jaw Closure of a Robotic Surgical System," filed on Apr. 30, 2021, published as U.S. Pub. No. 2022/0346897 on Nov. 3, 2022; U.S. patent application Ser. No. 17/245,340, entitled "Robotic Surgical System with an Articulation Lockout," filed on Apr. 30, 2021, published as U.S. Pub. No. 2022/0346891 on Nov. 3, 2022; U.S. patent application Ser. No. 17/245,351, entitled "Multi-Zone Jaw Closure of a Robotic Surgical System," filed on Apr. 30, 2021, published as U.S. Pub. No. 2022/0346898 on Nov. 3, 2022; and/or U.S. patent application Ser. No. 17/245,111, entitled "Selectable Jaw Closure of a Robotic Surgical System," filed on Apr. 30, 2021, published as U.S. Pub. No. 2022/0346890 on Nov. 3, 2022. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical instrument, comprising:
   (a) an end effector;
   (b) a shaft assembly extending proximally from the end effector, wherein the shaft assembly defines a longitudinal axis;
   (c) a first drive operatively connected to a first portion of at least one of the end effector or the shaft assembly, wherein the first drive is configured to longitudinally translate relative to the longitudinal axis from a first drive position toward a second drive position to respectively actuate the first portion from a first portion position toward a second portion position; and
   (d) an activating mechanism including an actuation body operatively connected to the first drive and configured to rotate from a first rotational body position toward a second rotational body position to selectively direct translation of the first drive from the first drive position toward the second drive position, and wherein the actuation body is further configured to translate relative to the longitudinal axis from a first translational body position toward a second translational body position to selectively direct translation of the first drive from the first drive position toward the second drive position.

2. The surgical instrument of claim 1, wherein the end effector includes a jaw, and wherein the first portion of at least one of the end effector or the shaft assembly includes the jaw of the end effector.

3. The surgical instrument of claim 2, wherein the end effector is configured to staple a tissue of a patient.

4. The surgical instrument of claim 3, wherein the jaw includes an anvil configured to deform a plurality of staples.

5. The surgical instrument of claim 1, wherein the shaft assembly includes an articulation section, and wherein the first portion of at least one of the end effector or the shaft assembly includes the articulation section of the shaft assembly.

6. The surgical instrument of claim 1, wherein the first drive includes a first follower, wherein the actuation body includes a cam slot, and wherein the first follower is received within the cam slot such that the cam slot guides movement of the first follower from the first drive position toward the second drive position as the actuation body rotates from the first rotational body position toward the second rotational body position.

7. The surgical instrument of claim 6, wherein the first follower is received within the cam slot such that the cam slot guides movement of the first follower from the first drive position toward the second drive position as the actuation body translates from the first translational body position toward the second translational body position.

8. The surgical instrument of claim 7, wherein the actuation body is a barrel cam having the cam slot, wherein the barrel cam is positioned on the longitudinal axis and configured to selectively rotate about the longitudinal axis, and wherein the barrel cam is further configured to selectively translate along the longitudinal axis.

9. The surgical instrument of claim 1, wherein the actuation body is configured to be rotationally locked relative to the longitudinal axis as the actuation body translates relative to the longitudinal axis.

10. The surgical instrument of claim 1, wherein the actuation body is configured to be translationally locked relative to the longitudinal axis as the actuation body rotates relative to the longitudinal axis.

11. The surgical instrument of claim 1, wherein the activating mechanism further includes a rotational driver and a translational driver, wherein the rotational driver is engaged with the actuation body and configured to selectively rotate the actuation body from the first rotational body position toward the second rotational body position, and wherein the translational driver is engaged with the actuation body and configured to selectively translate the actuation body from the first translational body position toward the second translational body position.

12. The surgical instrument of claim 11, wherein the rotational driver includes a drive gear and the actuation body includes a driven gear, wherein the first translational body position is a proximal-most position and the second translational body position is a distal-most position, and wherein the drive gear remains engaged with the driven gear in each of the proximal-most position and the distal-most position.

13. The surgical instrument of claim 11, wherein the translational driver includes a yoke engaged with the actuation body, and wherein the yoke remains engaged with the actuation body while rotating the actuation body.

14. The surgical instrument of claim 13, wherein the yoke includes a pin and the actuation body includes an annular channel, and wherein the pin is movably received within the annular channel such that the pin remains engaged with the actuation body while rotating the actuation body.

15. The surgical instrument of claim 13, wherein the translational driver includes a lever pivotally secured relative to the actuation body and configured to be selectively manipulated from a first lever position toward a second lever position thereby urging the actuation body from the first translational body position toward the second translational body position.

16. A surgical instrument, comprising:
(a) an end effector having a first jaw movably secured relative to a second jaw, wherein the first jaw is configured to move from a closed position toward an opened position;
(b) a shaft assembly extending proximally from the end effector, wherein the shaft assembly defines a longitudinal axis;
(c) a first drive including a first follower and operatively connected to the first jaw, wherein the first drive is configured to longitudinally translate relative to the longitudinal axis from a first drive position toward a second drive position to respectively actuate the first jaw from the closed position toward the opened position; and
(d) an activating mechanism including an actuation body configured to rotate from a first rotational body position toward a second rotational body position, wherein the actuation body has a cam slot, wherein the first follower is received within the cam slot such that the cam slot guides movement of the first follower from the first drive position toward the second drive position as the actuation body rotates from the first rotational body position toward the second rotational body position, wherein the actuation body is further configured to translate relative to the longitudinal axis from a first translational body position toward a second translational body position such that the cam slot guides movement of the first follower from the first drive position toward the second drive position as the actuation body translates from the first translational body position toward the second translational body position, wherein the actuation body is configured to be rotationally locked relative to the longitudinal axis as the actuation body translates relative to the longitudinal axis, and wherein the actuation body is configured to be translationally locked relative to the longitudinal axis as the actuation body rotates relative to the longitudinal axis.

17. The surgical instrument of claim 16, wherein the activating mechanism further includes a rotational driver and a translational driver, wherein the rotational driver is engaged with the actuation body and configured to selectively rotate the actuation body from the first rotational body position toward the second rotational body position, and wherein the translational driver is engaged with the actuation body and configured to selectively translate the actuation body from the first translational body position toward the second translational body position.

18. The surgical instrument of claim 17, wherein the rotational driver includes a drive gear and the actuation body includes a driven gear, wherein the first translational body position is a proximal-most position and the second translational body position is a distal-most position, and wherein the drive gear remains engaged with the driven gear in each of the proximal-most position and the distal-most position.

19. The surgical instrument of claim 18, wherein the translational driver includes a yoke engaged with the actuation body, wherein the yoke remains engaged with the actuation body while rotating the actuation body, wherein the yoke includes a pin and the actuation body includes an annular channel, and wherein the pin is movably received within the annular channel such that the pin remains engaged with the actuation body while rotating the actuation body.

20. A method of actuating a first portion of at least one of an end effector or a shaft assembly of a surgical instrument, wherein the surgical instrument includes (a) the end effector; (b) the shaft assembly extending proximally from the end effector, wherein the shaft assembly defines a longitudinal axis; (c) a first drive operatively connected to the first portion of at least one of the end effector or the shaft assembly, wherein the first drive is configured to longitudinally translate relative to the longitudinal axis from a first drive position toward a second drive position to respectively actuate the first portion from a first portion position toward a second portion position; and (d) an activating mechanism including an actuation body operatively connected to the first drive and configured to rotate from a first rotational body position toward a second rotational body position to selectively direct translation of the first drive from the first drive position toward the second drive position, and wherein the actuation body is further configured to translate relative to the longitudinal axis from a first translational body position toward a second translational body position to selectively direct translation of the first drive from the first drive position toward the second drive position, the method comprising:

(a) translating the actuation body while simultaneously inhibiting rotation of the actuation body to direct translation of the first drive from the first drive position toward the second drive position thereby actuating the first portion from the first portion position toward the second portion position.

* * * * *